(12) United States Patent
Perner et al.

(10) Patent No.: US 10,821,067 B2
(45) Date of Patent: *Nov. 3, 2020

(54) HAIR-TREATMENT COMPOSITIONS COMPRISING A POLYURETHANE LATEX POLYMER AND THICKENING AGENT

(71) Applicant: L'OREAL, Paris (FR)

(72) Inventors: Allison Perner, Metuchen, NJ (US); Anand Mahadeshwar, Scotch Plains, NJ (US); Marie Huynh, Monmouth Junction, NJ (US); Lindsay Menzer, Randolph, NJ (US); Azizah Khader Suleiman, Paterson, NJ (US); Lisa Chuyin Ye-Tse, Brooklyn, NY (US); Vanessa Decarlo, Roselle Park, NJ (US)

(73) Assignee: L'OREAL, Paris (FR)

( * ) Notice: Subject to any disclaimer, the term of this patent is extended or adjusted under 35 U.S.C. 154(b) by 166 days.

This patent is subject to a terminal disclaimer.

(21) Appl. No.: 15/691,041

(22) Filed: Aug. 30, 2017

(65) Prior Publication Data

US 2018/0311140 A1   Nov. 1, 2018

Related U.S. Application Data

(60) Provisional application No. 62/491,841, filed on Apr. 28, 2017.

(51) Int. Cl.
*A61K 8/87* (2006.01)
*A61Q 5/00* (2006.01)
(Continued)

(52) U.S. Cl.
CPC ............ *A61K 8/87* (2013.01); *A61K 8/042* (2013.01); *A61K 8/06* (2013.01); *A61K 8/062* (2013.01);
(Continued)

(58) Field of Classification Search
CPC . A61K 8/87; A61K 8/89; A61K 8/891; A61K 8/062; A61K 8/064; A61K 8/604;
(Continued)

(56) References Cited

U.S. PATENT DOCUMENTS 6,358,502 B1   3/2002  Tanabe et al.
6,585,965 B1 * 7/2003  Carballada ............... A61K 8/06
                                                                424/70.1
(Continued)

FOREIGN PATENT DOCUMENTS

DE   102009054516 A1   6/2011
DE   102010063923 A1   6/2012
(Continued)

OTHER PUBLICATIONS

Sephora—Perfect Hair Day In-Shower Styler—Living Proof Apr. 28, 2017.
(Continued)

*Primary Examiner* — Lakshmi S Channavajjala
(74) *Attorney, Agent, or Firm* — Polsinelli PC

(57) ABSTRACT

The instant disclosure relates to hair-treatment compositions. The hair-treatment compositions typically include: one or more polyurethane latex polymers; one or more thickening agents; one or more water-soluble solvents; and water. Additional components such as silicones, emulsifiers, surfactants, cationic polymers, etc., can also be included. The instant disclosure also relates to kits that include the hair-treatment compositions and to methods for treating hair with the hair-treatment compositions.

10 Claims, 4 Drawing Sheets

(51) Int. Cl.
| | |
|---|---|
| *A61K 8/89* | (2006.01) |
| *A61K 8/04* | (2006.01) |
| *A61K 8/06* | (2006.01) |
| *A61K 8/891* | (2006.01) |
| *A61K 8/73* | (2006.01) |
| *A61K 8/81* | (2006.01) |
| *A61K 8/892* | (2006.01) |
| *A61K 8/898* | (2006.01) |
| *A61K 8/895* | (2006.01) |
| *A61K 8/34* | (2006.01) |
| *A61K 8/31* | (2006.01) |
| *A61K 8/92* | (2006.01) |
| *A61K 8/60* | (2006.01) |
| *A61K 8/86* | (2006.01) |
| *A61K 8/46* | (2006.01) |
| *A61K 8/37* | (2006.01) |
| *A61Q 5/06* | (2006.01) |
| *A61K 8/58* | (2006.01) |
| *A61K 8/44* | (2006.01) |
| *A61K 8/68* | (2006.01) |

(52) U.S. Cl.
CPC ............... *A61K 8/064* (2013.01); *A61K 8/31* (2013.01); *A61K 8/342* (2013.01); *A61K 8/345* (2013.01); *A61K 8/347* (2013.01); *A61K 8/37* (2013.01); *A61K 8/375* (2013.01); *A61K 8/44* (2013.01); *A61K 8/463* (2013.01); *A61K 8/585* (2013.01); *A61K 8/602* (2013.01); *A61K 8/604* (2013.01); *A61K 8/68* (2013.01); *A61K 8/731* (2013.01); *A61K 8/732* (2013.01); *A61K 8/737* (2013.01); *A61K 8/8111* (2013.01); *A61K 8/8164* (2013.01); *A61K 8/86* (2013.01); *A61K 8/89* (2013.01); *A61K 8/891* (2013.01); *A61K 8/892* (2013.01); *A61K 8/895* (2013.01); *A61K 8/898* (2013.01); *A61K 8/92* (2013.01); *A61K 8/922* (2013.01); *A61K 8/927* (2013.01); *A61Q 5/00* (2013.01); *A61Q 5/06* (2013.01); *A61K 2800/48* (2013.01); *A61K 2800/594* (2013.01)

(58) Field of Classification Search
CPC ...... A61K 8/731; A61K 8/8164; A61K 8/737; A61K 8/732
See application file for complete search history.

(56) References Cited

U.S. PATENT DOCUMENTS

| | | | |
|---|---|---|---|
| 7,226,580 B2 | 6/2007 | Amalric et al. | |
| 8,920,787 B2* | 12/2014 | Li | A61K 8/8152 |
| | | | 424/70.11 |
| 2001/0009659 A1* | 7/2001 | Pratley | A61K 8/046 |
| | | | 424/45 |
| 2009/0060858 A1 | 3/2009 | Schwarzwaelder et al. | |
| 2014/0342968 A1 | 11/2014 | Hourigan et al. | |
| 2015/0004114 A1* | 1/2015 | Tan | A61K 8/87 |
| | | | 424/70.13 |
| 2015/0004116 A1 | 1/2015 | Tan et al. | |
| 2015/0004117 A1 | 1/2015 | Tan et al. | |
| 2015/0004119 A1 | 1/2015 | Tan et al. | |
| 2015/0174056 A1* | 6/2015 | Barba | A61K 8/361 |
| | | | 424/70.7 |
| 2016/0175233 A1 | 6/2016 | Mark et al. | |
| 2016/0175237 A1 | 6/2016 | Perner et al. | |
| 2016/0175238 A1 | 6/2016 | Shin et al. | |

FOREIGN PATENT DOCUMENTS

| | | |
|---|---|---|
| EP | 2105127 A1 | 9/2009 |
| WO | WO-2012084339 A2 | 6/2016 |
| WO | WO-2016100885 A1 | 6/2016 |

OTHER PUBLICATIONS

International Search Report and Written Opinion dated Jul. 10, 2018 for corresponding PCT Application No. PCT/US2018/029817.
Database GNPD Mintel, "Air Dry It Un-Done Style," Mar. 2017, pp. 1-2.
Database GNPD Mintel, "Curly Hair Conditioner," Feb. 2015, pp. 1.
Database GNPD Mintel, "Defining Style Cream," Jul. 2015, pp. 1-6.
Database GNPD Mintel, "230° Heat Protection Spray," Mar. 2017, pp. 1-4.
Database GNPD Mintel, "Sold Out Curl Priming," Feb. 2017, pp. 1-2.

* cited by examiner

HAIR-TREATMENT COMPOSITIONS COMPRISING A POLYURETHANE LATEX POLYMER AND THICKENING AGENT

CROSS-REFERENCE TO RELATED APPLICATIONS

This application is a Non-Provisional application of U.S. Provisional Application No. 62/491,841, filed Apr. 28, 2017. The entire contents are incorporated herein by reference.

FIELD OF THE DISCLOSURE

The instant disclosure relates to hair-treatment compositions, which are particularly useful for improving hair manageability, imparting long-lasting style and frizz control to hair, and for protecting hair from damage. Also disclosed are kits that include the hair-treatment compositions and methods for using the hair-treatment compositions.

BACKGROUND

For decades, consumers have used hair styling products to help achieve a desired look, including fuller/thicker hair, sleek and straight hair, and frizz-free defined curls. Many different types of hair styling products are commercially available. Nonetheless, consumers desire new multi-functional hair products that are long lasting, convenient, and impart certain cosmetic characteristics to the hair.

Traditional anhydrous oil treatments have been used to nourish and moisturize dull, dry, and damaged hair. These oil treatments also help control frizz and define hair while maintaining a natural look, but the performance of oil treatments is limited, especially in terms of long lasting shape control. In particular, traditional oil treatments do not typically provide benefits such as shaping memory, improved volume, strengthening, heat protection, etc. Oil treatments moisturize and control frizz while maintaining a natural look, but lack many additional styling benefits that consumers seek.

Styling products that provide styling benefits such as shaping memory, hold, improved volume, etc. are advertised but these products also suffer from certain drawbacks. For example, many styling products provide protection against external factors such as protection from moisture to minimize or reduce frizziness. To protect against moisture, a water-resistant film or coating can be applied to the hair. Many of these films or coatings are formed with film-forming polymers. Depending on the chemical make-up of the film-forming polymers, they may be either soluble in water, or they may be water insoluble polymers that are solubilized in water via various chemical modifications, such as neutralization. Solutions comprising these polymers tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or "crunchy" feeling (i.e. the films become hard and brittle and therefore have a crunchy feel or sound when manipulated), which is undesirable to many consumers.

Consumers desire new multi-functional hair products that have a natural look and feel, impart good styling benefits to hair, are durable, and lack the drawbacks of other products.

SUMMARY OF THE DISCLOSURE

The instant disclosure relates to hair-treatment compositions that include a unique combination of components that function to impart desirable cosmetic properties to the hair. For example, the hair-treatment compositions are useful for improving hair manageability, imparting long-lasting style and frizz control to hair, and for protecting hair from damage, especially heat damage. Also, consumers find the natural look and feel of hair treated with the compositions to be very appealing. The hair-treatment compositions typically include at least:

one or more polyurethane latex polymers;
one or more thickening agents; and
water.

Additional components such as thickening agents, silicones, emulsifiers, surfactants, cationic polymers, etc., can also be included. While not wishing to be bound by any particular theory, the inventors believe that the compositions provide the hair with a hydrophobic, flexible, film or film-like coating that is long-lasting, has a very natural look and feel, and improves the styling properties of the hair. The hydrophobic film or film-like coating also provides protection to the hair from damage, for example, damage caused by heat, environmental stress, etc. Furthermore, the film or film-like coating is long lasting, as it can survive repeated washings. Thus, hair maintains the desirable cosmetic properties imparted by the hair-treatment compositions despite subsequent shampooing, rinsing, etc.

The hair-treatment compositions can be used at home during an individual's regular shampooing and/or conditioning routine and therefore do not require special procedures that are only available at professional salons. Accordingly, the instant disclosure also relates to kits that include a hair-treatment composition of the instant disclosure. The kits typically include at least one hair-treatment composition according to the instant disclosure (a hair-treatment composition comprising one or more polyurethane latex polymers, one or more thickeners, one or more water-soluble solvents, and water, etc.) and one or more additional hair-treatment compositions, for example, a shampoo, a conditioner, etc. The various hair-treatment compositions are separately contained in the kits. In some instances, the kits include one or more hair-treatment compositions (according the instant disclosure), a shampoo, and/or a conditioner, all of which are separately contained.

Finally, as mentioned previously, the hair-treatment compositions are unique in their ability to provide hair with improved manageability, long-lasting style and frizz control, and protection. Accordingly, the instant disclosure relates to methods for treating hair, for example, for improving the manageability of hair, for imparting lasting style and frizz control, and for protecting the hair from damage, such as heat damage. More specifically, the hair-treatment compositions may be used in methods for conditioning the hair, providing curl definition to the hair, providing frizz control to the hair, improving ease of combability and detangling, protecting the hair from damage, including heat damage, and increasing the appearance of hair volume.

The methods of treating hair according to the disclosure include methods according to various routines. For instance, the hair-treatment composition may be mixed with a shampoo (or conditioner) prior to application to the hair. Alternatively, the hair-treatment composition may be layered on top of (or lathered into) hair to which the shampoo (or conditioner) is already applied. Furthermore, the hair-treatment composition may be applied separate from the shampoo (or conditioner), i.e., applied to the hair after the shampoo (or conditioner) has been rinsed from the hair.

BRIEF DESCRIPTION OF THE DRAWINGS

Implementations of the present technology will now be described, by way of example only, with reference to the attached figures, wherein.

DETAILED DESCRIPTION OF THE DISCLOSURE

Figure 1:
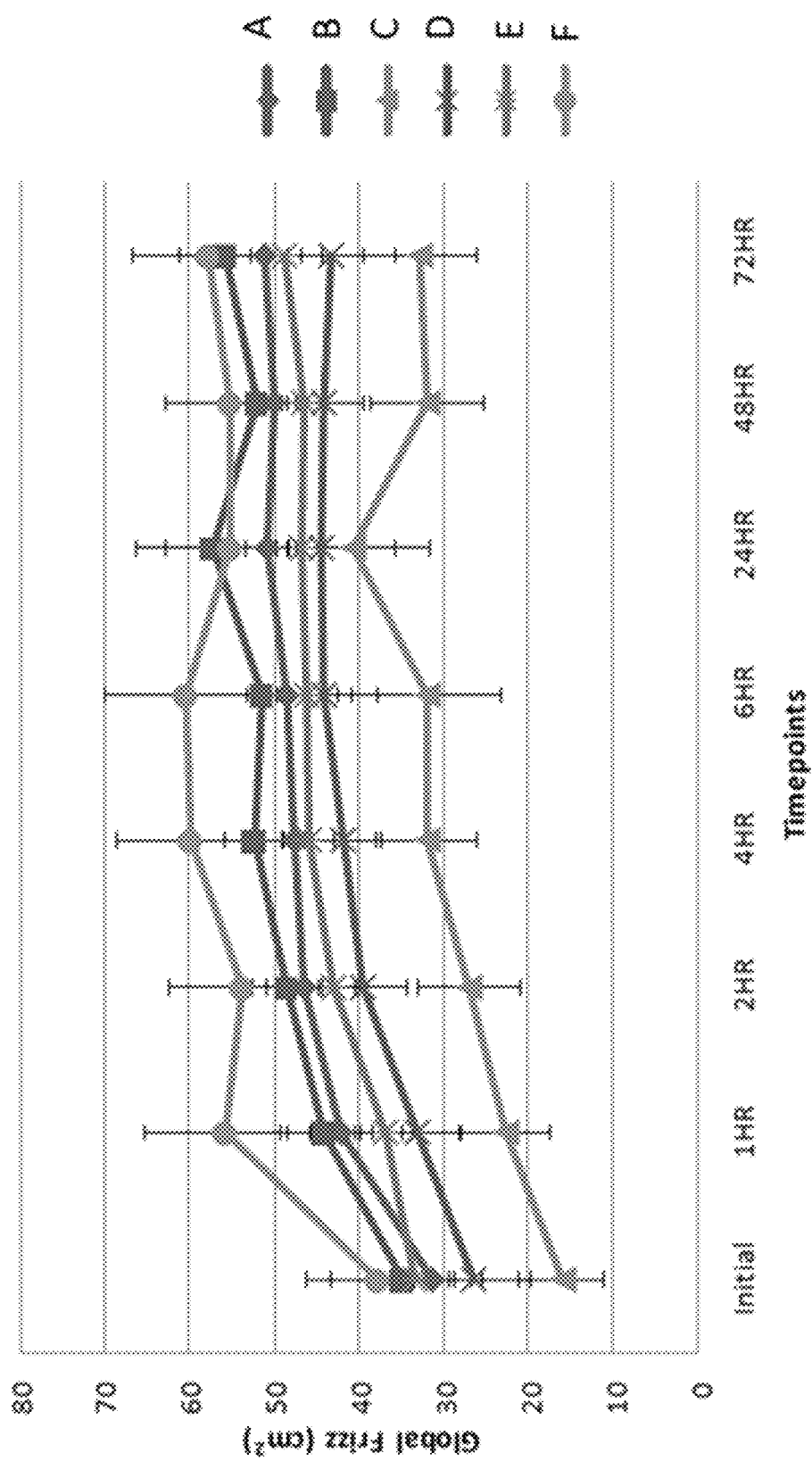
FIG. 1 plots global frizz scores over time for (A) control hair tresses; (B) tresses treated with a standard shampoo and conditioner; (C) tresses treated with Inventive Formulation #1; (D) tresses treated with a standard shampoo and standard conditioner in conjunction with Inventive Formulation #1; (E) tresses treated with a commercial benchmark product; and (F) tresses treated with a commercial shampoo and commercial conditioner in conjunction with a commercial benchmark product.

The instant disclosure relates to hair-treatment compositions. The term "treatment" in the context of a "hair-treatment" composition encompasses many types of compositions for application to the hair, for example, shampoos, conditioners, hair-rinses, hair lotions, hair gels, mouse-type products, sprays, etc. A hair-treatment composition is characterized by its ability to provide a cosmetic benefit to the hair. As is well-known, a shampoo provides cleansing benefits the hair, a conditioner provides conditioning benefits to the hair, and a gel can provide styling benefits to the hair. Non-limiting examples of additional benefits that can be imparted to hair include frizz control, smoothness, ease of combability, fullness and body, shine, strengthening, damage repair or resistance to damage, including resistance to heat damage, enhancing luster or color, etc.

The hair-treatment compositions of the instant disclosure may include:
one or more polyurethane latex polymers;
one or more thickening agents;
one or more water soluble solvents; and
water.

The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly well-suited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the hair-treatment composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

Non-limiting examples of thickening agents that may be used in the hair-treatment compositions include carboxylic acid/carboxylate copolymers, hydrophobically-modified cross-linked copolymers of carboxylic acid and alkyl carboxylate vinyl polymers, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, polyethyleneimine, bentonite, aluminum magnesium silicate, laponite, hectonite, anhydrous silicic acid, and a mixture thereof. In some cases, the one or more thickening agents are selected from the group consisting of cross linked acrylic acid polymers (carbomer), methyl cellulose, ethyl cellulose, hydroxyethyl cellulose, hydroxypropyl methyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof.

The total amount of the one or more thickening agents can vary but is typically about 0.01 to about 10 wt. %, based on the total weight of the hair-treatment composition. The total amount of the one or more thickening agents may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, or about 0.5 to about 5 wt. %.

The hair-treatment compositions may include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%. Non-limiting examples of water-soluble solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, propylene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

A more exhaustive list of water-soluble solvents that may be included in the hair-treatment compositions is provided later, under the heading "Water-Soluble Solvents."

The total amount of the one or more water-soluble solvents (which is separate than the water in the compositions) may vary, but in some cases are about 0.1 to about 60 wt. %, based on the total weight of the hair-treatment composition. The total amount of the one or more water-soluble solvents may be about 0.1 to about 55 wt. %, about 0.1 to about 50 wt. %, about 0.1 to about 45 wt. %, about 0.1 to about 60 wt. %, about 0.1 to about 55 wt. %, about 0.1 to about 50 wt. %, about 0.1 to about 50 wt. %, about 1 to about 60 wt. %, about 1 to about 55 wt. %, about 1 to about 50 wt. %, about 5 to about 60 wt. %, about 5 to about 55 wt. %, about 10 to about 50 wt. %, or about 0.1 to about 10 wt. %, about 0.1 to about 5 wt. %.

One or more silicones may be included in the hair-treatment compositions. Non-limiting examples of silicones include polyorganosiloxanes, polyalkylsiloxanes, polyarylsiloxanes, polyalkarylsiloxanes, polyestersiloxanes, and a mixture thereof. In particular, suitable examples of silicones include dimethicone, cyclomethicone, amodimethicone, trimethyl silyl amodimethicone, phenyl trimethicone, trimethyl siloxy silicate, and mixtures thereof. For example, in some cases, the hair-treatment compositions may include dimethicone, lauryl PEG/PPG-18/18 methicone, dimethiconol, amodimethicone, cyclomethicone, and a mixture thereof. A more exhaustive list of silicones that may be included in the hair-treatment compositions is provided later, under the heading "Silicones."

The total amount of the one or more silicones may vary but is typically about 0.01 to about 40 wt. %, based on the total weight of the hair-treatment composition. In some cases, the total amount of the one or more silicones is about 0.01 to about 30 wt. %, about 0.01 to about 20 wt. %, about 0.01 to about 15 wt. %, 0.01 to about 10 wt. %, about 0.01 to about 8 wt. %, about 0.01 to about 5 wt. %, about 0.1 to about 40 wt. %, about 0.1 to about 30 wt. %, about 0.1 to about 20 wt. %, about 0.1 to about 15 wt. %, about 0.1 to about 10 wt. %, or about 0.1 to about 5 wt. %.

The above hair-treatment compositions may be in a variety of different forms, for example, a gel, a lotion, a cream, an aerated product (e.g., a mousse), etc. For example, in a specific embodiment, the hair-treatment composition is a gel comprising:

about 0.01 to about 10 wt. %, about 0.1 to about 10 wt. %, or about 1 to about 5 wt. % of polyurethane-34;

about 0.01 to about 10 wt. %, about 0.1 to about 8 wt. %, or about 0.1 to about 5 wt. % of one or more thickening agents, for example, one or more thickening agents selected from the group consisting of selected from the group consisting of cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;

about 0.01 to about 60 wt. %, about 0.1 to about 55 wt. %, or about 0.1 to about 50 wt. % of one or more water-soluble solvents, for example, one or more water-soluble solvents are selected from the group consisting of polyhydric alcohols, glycol ethers, $C_{1-4}$ alcohols, and a mixture thereof;

optionally, about 0.01 to about 30 wt. %, about 1 to about 25 wt. %, or about 5 to about 25 wt. % of one or more silicones, for example, silicones selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof; and about 15 to about 90 wt. % of water.

In one embodiment, the hair-treatment compositions include:
one or more polyurethane latex polymers;
one or more thickening agents;
one or more emulsifiers;
one or more fatty compounds; and
water.

The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly well-suited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the hair-treatment composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

Non-limiting examples of thickening agents that may be used in the hair-treatment compositions include carboxylic acid/carboxylate copolymers, hydrophobically-modified cross-linked copolymers of carboxylic acid and alkyl carboxylate vinyl polymers, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, polyethyleneimine, bentonite, aluminum magnesium silicate, laponite, hectonite, anhydrous silicic acid, and a mixture thereof. In some cases, the one or more thicking agents are selected from the group consisting of cross linked acrylic acid polymers (carbomer), methyl cellulose, ethyl cellulose, hydroxyethyl cellulose, hydroxypropyl methyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof.

The total amount of the one or more thickening agents can vary but is typically about 0.01 to about 10 wt. %, based on the total weight of the hair-treatment composition. The total amount of the one or more thickening agents may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, or about 0.5 to about 5 wt. %.

These hair-treatment compositions include one or more emulsifiers (and are often in the form of an emulsion). Non-limiting examples of emulsifiers include alkylpolyglycosides, glyceryl esters, ethylene glycol esters, propylene glycol esters and sucrose esters of fatty acids, ethoxylated fatty alcohols, ethoxylated fatty acids, partial glycerides of ethoxylated fatty acids, polyglycerolated fatty acid triglycerides and their ethoxylated derivatives, and a mixture thereof. In some cases, alkylpolyglycosides are useful, in particular octyldodecyl xyloside, cetearyl glucoside, isostearyl glucoside, and mixtures thereof. Alkylpolyglucosides may be used with a coemulsifier, more especially with a fatty alcohol and/or a fatty acid (fatty compounds of the instant disclosure) and especially a fatty alcohol containing the same fatty chain as that of the alkylpolyglucoside, i.e. comprising from 14 to 24 carbon atoms and containing a branched and/or unsaturated chain, for example isostearyl alcohol when the alkylpolyglucoside is isostearyl glucoside, and oleyl alcohol when the alkylpolyglucoside is oleyl glucoside, and octyldodecanol when the alkylpolyglucoside is octyldodecyl xyloside.

In some cases, nonionic emulsifiers may be used. Non-limiting examples of nonionic emulsifiers include glyceryl esters, ethylene glycol esters, propylene glycol esters and sucrose esters of fatty acids, such as: glyceryl caprate, glyceryl lanolate, glyceryl myristate, glyceryl laurate, glyceryl dilaurate, glyceryl monostearate, glyceryl monohydroxy stearate, glyceryl stearate, glyceryl stearate citrate, glycol stearate, glycol distearate, glycol dilaurate, diethylene glycol dilaurate, propylene glycol stearate, propylene glycol laurate, propylene glycol distearate, palm glycerides, hydrogenated coco glycerides, sucrose distearate, and a mixture thereof. Another useful class of non-ionic emulsifiers is polyethylene esters of fatty acids, fatty acid glycerides and sorbitan esters and with ethylene groups ranging from 5 to 150. Examples include: PEG-8 stearate, PEG-9 stearate, PEG-8 distearate, PEG-20 stearate, PEG-30 stearate, PEG-40 stearate, EG-50 stearate, PEG-100 stearate, PEG-150 laurate, PEG-30 glyceryl stearate, PEG-25 glyceryl trioleate, PEG-15 glyceryl ricinoleate, PEG-20 glyceryl stearate, PEG-20 glyceryl isostearate, PEG-20 glyceryl oleate, PEG-20 glyceryl laurate, PEG-30 stearate, PEG-30 glyceryl stearate, PEG-40 sorbitan lanolate, PEG-6 sorbitan beeswax, PEG-20 sorbitan beeswax, and a mixture thereof. Yet another useful class of non-ionic emulsifiers is represented by ethoxylated fatty alcohols with ethylene groups ranging from 2 to 30. Other nonionic emulsifiers may include sorbitan monoesters like sorbitan stearate, sorbitan tristearate, sorbitan palmitate, sorbitan laurate, cholesterol, lanolin, phytosterols, lecithin and hydrogenated lecithin.

A more exhaustive list of emulsifiers that may be included in the hair-treatment compositions is provided later, under the heading "Emulsifiers."

The total amount of the one or more emulsifiers can vary but is typically about 0.1 to about 15 wt. %, based on the total weight of the hair-treatment composition. In some cases, the total amount of the one or more emulsifiers may be about 0.1 to about 12 wt. %, about 0.1 to about 10 wt. %, about 0.1 to about 8 wt. %, about 0.1 to about 5 wt. %, about 0.5 to about 15 wt. %, about 0.5 to about 12 wt. %, about 0.5 to about 10 wt. %, about 0.5 to about 8 wt. %, about 0.5 to about 5 wt. %, or about 1 to about 5 wt. %.

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of C13-16 isoparaffin, PEG-40 hydrogenated castor oil, isononyl isnonoanoate, hydrogenated polyisobutene, beeswax, shea butter, cetearyl alcohol, cetyl esters, isononanoate, and a mixture thereof.

A more exhaustive list of fatty compounds that may be included in the hair-treatment compositions is provided later, under the heading "Fatty Compounds."

The total amount of the one or more fatty compounds can vary but is typically about 1 to about 40 wt. %, based on the total weight of the hair-treatment composition. In some cases, the total amount of the one or more fatty compounds may be about 0.5 to about 30 wt. %, about 0.5 to about 25 wt. %, about 0.5 to about 20 wt. %, about 0.5 to about 15 wt. %, about 0.5 to about 10 wt. %, about 1 to about 30 wt. %, about 1 to about 25 wt. %, about 1 to about 20 wt. %, about 1 to about 15 wt. %, or about 1 to about 10 wt. %.

In a more specific embodiment, the hair-treatment composition is an emulsion comprising:
  about 0.01 to about 10 wt. %, about 0.1 to about 10 wt. %, or about 1 to about 5 wt. % of polyurethane-34;
  about 0.01 to about 10 wt. %, about 0.1 to about 8 wt. %, or about 0.1 to about 5 wt. % of one or more thickening agents, for example, thickening agents selected from the group consisting of selected from the group consisting of cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;
  about 0.1 to about 15 wt. %, about 0.1 to 10, or about 0.1 to about 8 wt. % of one or more emulsifiers selected from the group consisting of alkylpolyglycosides, glyceryl esters, ethylene glycol esters, propylene glycol esters and sucrose esters of fatty acids, ethoxylated fatty alcohols, ethoxylated fatty acids, partial glycerides of ethoxylated fatty acids, polyglycerolated fatty acid triglycerides, and a mixture thereof;
  about 1 to about 40 wt. %, about 1 to about 30 wt. %, or about 1 to about 20 wt. % of one or more fatty compounds, for example, fatty compounds selected from the group consisting of C13-14 isoparaffin, isononyl isonanoate, hydrogenated polyisobutene, shea butter, cetearyl alcohol, cetyl esters, isononanoat, and a mixture thereof; and
  water.

In some instances, the hair-treatment composition is a water-in-oil emulsion. Emulsifiers appropriate for use in water-in-oil emulsions are described throughout the instant disclosure. Nonetheless, in some cases, a water-in-oil emulsion includes one or more alkylpolyglycosides. A particularly well suited alkylpolyglycoside for use in water-in-oil emulsions comprising high amounts of an aqueous phase is octyldodecyl xyloside. This emulsifier may be used with a coemulsifer, such as octyldodecanol (a fatty compound). A more exhaustive list of emulsifiers that may be included in the water-in-oil emulsions is provided later, under the heading "Emulsifiers."

The total amount of water in these water-in-oil emulsions can vary but is typically about 60 wt. % to about 90 wt. %, based on the total weight of the hair-treatment composition. The total amount of water may be about 65 wt. % to about 90 wt. %, about 70 wt. % to about 90 wt. %, about 60 to about 85 wt. %, about 65 to about 85 wt. %, or about 70 to about 85 wt. %.

A non-limiting embodiment of a water-in-oil emulsion includes:
  about 0.01 to about 10, about 0.1 to about 10, or about 0.1 to about 5 wt. % of polyurethane-34;
  about 0.01 to about 10 wt. %, about 0.1 to about 8 wt. %, or about 0.1 to about 5 wt. % of one or more thickening agents selected from the group consisting of selected from the group consisting of polyacrylamide, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;
  about 0.1 to about 10 wt. %, about 0.1 to about 8 wt. %, or about 0.1 to about 5 wt. % of one or more emulsifiers, wherein the one or more emulsifiers comprise one or more alkylpolyglycosides, in particular octyldodecyl xyloside;
  about 1 to about 40 wt. %, about 1 to about 30, or about 5 to about 25 wt. % of one or more fatty compounds selected from the group consisting of C13-14 isoparaffin, isononyl isonanoate, hydrogenated polyisobutene, shea butter, cetearyl alcohol, and cetyl esters, isononanoate, and a mixture thereof; and
  about 60 wt. % to about 90 wt. %, about 65 to about 90 wt. %, or about 70 to about 90 wt. % of water.

In some instances, the hair-treatment composition is an oil-in-water emulsion. Non-limiting examples of emulsifiers that may be used in oil-in-water emulsions are provided throughout the disclosure. Nonetheless, non-limiting examples include alkylpolyglycosides, glyceryl esters, ethylene glycol esters, propylene glycol esters and sucrose esters of fatty acids, ethoxylated fatty alcohols, ethoxylated fatty acids, partial glycerides of ethoxylated fatty acids, polyglycerolated fatty acid triglycerides and their ethoxylated derivatives, and a mixture thereof. A more exhaustive list of emulsifiers that may be included in the oil-in-water compositions is provided later, under the heading "Emulsifiers."

The total amount of water in these water-in-oil emulsions can vary but is typically about 50 wt. % to about 80 wt. %, based on the total weight of the hair-treatment composition. The total amount of water may be about 55 wt. % to about 80 wt. %, about 60 wt. % to about 80 wt. %, about 50 to about 85 wt. %, about 55 to about 85 wt. %, or about 60 to about 80 wt. %.

A non-limiting embodiment of an oil-in-water emulsion includes:
  about 0.01 to about 10, about 0.1 to about 10, or about 0.1 to about 5 wt. % of polyurethane-34;
  about 0.01 to about 10 wt. %, about 0.1 to about 8 wt. %, or about 0.1 to about 5 wt. % of one or more thickening agents selected from the group consisting of selected from the group consisting of polyacrylamide, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;

about 0.1 to about 10 wt. %, about 0.1 to about 8 wt. %, or about 0.1 to about 5 wt. % of one or more emulsifiers selected from the group consisting of glyceryl stearate, cetearyl glucoside, and a mixture thereof;

about 1 to about 40 wt. % of one or more fatty compounds selected from the group consisting of C13-14 isoparaffin, isononyl isononanoate, hydrogenated polyisobutene, shea butter, cetearyl alcohol, and cetyl esters, and a mixture thereof; and about 50 wt. % to about 80 wt. % of water.

In one embodiment, the hair-treatment compositions include:
one or more polyurethane latex polymers;
one or more thickening agents;
one or more amphoteric surfactants; and
water.

The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly well-suited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the hair-treatment composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

Non-limiting examples of thickening agents that may be used in the hair-treatment compositions include carboxylic acid/carboxylate copolymers, hydrophobically-modified cross-linked copolymers of carboxylic acid and alkyl carboxylate vinyl polymers, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, polyethyleneimine, bentonite, aluminum magnesium silicate, laponite, hectonite, anhydrous silicic acid, and a mixture thereof. In some cases, the one or more thicking agents are selected from the group consisting of cross linked acrylic acid polymers (carbomer), methyl cellulose, ethyl cellulose, hydroxyethyl cellulose, hydroxypropyl methyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof. A more exhaustive list of thickening agents that may be included in the hair-treatment compositions is provided later, under the heading "Thickening Agents."

The total amount of the one or more thickening agents can vary but is typically about 0.01 to about 10 wt. %, based on the total weight of the hair-treatment composition. The total amount of the one or more thickening agents may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, or about 0.5 to about 5 wt. %.

Amphoteric surfactants are well-known and may be used in the instant hair-treatment compositions. Non-limiting examples of amphoteric surfactants include betaines, sultaines, amphoacetates, amphoproprionates, and a mixture thereof. In some cases, one or more amphoproprionates may be used. A more exhaustive list of amphoteric surfactants that may be included in the hair-treatment compositions is provided later, under the heading "Amphoteric Surfactants."

The total amount of the one or more amphoteric surfactants may vary but is typically about 0.1 to about 25 wt. %, based on the total weight of the hair-treatment composition, including all ranges and subranges therebetween. Additionally, the total amount of the one or more amphoteric surfactants may be about 0.1 to about 20 wt. %, about 0.1 to about 15 wt. %, about 1 to about 25 wt. %, about 1 to about 20 wt. %, about 1 to about 15 wt. %, or about 5 to about 15 wt. %.

In some cases, the hair-treatment compositions may include one or more cationic polymers. Non-limiting examples of cationic polymers include poly(methacryloyloxyethyl trimethylammonium chloride), polyquaternium-37, quaternized cellulose derivatives, polyquaternium-4, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof. In some cases, the one or more cationic polymers are polyquaterniums, for example, polyquaternium-11, polyquaternium-37, etc.

The total amount of the one or more cationic polymers may vary but it typically about 0.01 to about 10 wt. %, based on the total weight of the hair-treatment compositions. The total amount of the one or more cationic polymers may be about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, or about 0.1 to about 3 wt. %.

In a more specific embodiment, the hair-treatment composition is lotion comprising:
about 0.01 to about 10 wt. % of polyurethane-34;
about 0.01 to about 10 wt. %, about 0.1 to about 10 wt. %, or about 1 to about 5 wt. % of polyurethane-34;
about 0.01 to about 10 wt. %, about 0.1 to about 8 wt. %, or about 0.1 to about 5 wt. % of one or more thickening agents, for example, thickening agents selected from the group consisting of selected from the group consisting of cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof about 0.1 to about 20 wt. %, about 1 to about 20 wt. %, or about 1 to about 15 wt. % of one or more amphoteric surfactants, for example, amphoteric surfactants selected from the group consisting of betaines, sultaines, amphoacetates, taurates, amphoproprionates, and a mixture thereof.

about 0.1 to about 20 wt. %, about 0.1 to about 10, or about 1 to about 8 wt. % of one or more water-soluble solvents selected from the group consisting of polyhydric alcohols, glycol ethers, $C_{1-4}$ alcohols, and a mixture thereof; and about 50 to about 90 wt. % of water.

The hair-treatment compositions of the instant disclosure may be incorporated into a kit. For example, the kits may include at least one hair-treatment composition according to the instant disclosure (a hair-treatment composition comprising one or more polyurethane latex polymers, one or more thickeners, one or more water-soluble solvents, and water, etc.) and one or more additional hair-treatment compositions, for example, a shampoo, a conditioner, etc. The various hair-treatment compositions are separately contained in the kits. In some instances, the kits include one or more hair-treatment compositions (according the instant disclosure), a shampoo, and/or a conditioner, all of which are separately contained. The kits may also include one or more hair-treatment compositions (according the instant disclosure), a shampoo, and a conditioner. Instructions, mixing components, brushes, gloves, measuring tools, etc., may also optionally be included in the kits.

The hair-treatment compositions may be packaged in a variety of different containers, such as, for example, a ready-to-use container. Non-limiting examples of useful packaging include tubes, jars, caps, unit dose packages, and bottles, including squeezable tubes and bottles. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a hair-treatment composition according to the instant disclosure, and the other tube may include a composition to be used with the hair-treatment composition, for example, a shampoo, a conditioner, an all-in-one shampoo/conditioner (i.e., a conditioning shampoo; also referred to as a "co-wash"). Both the hair-treatment composition and the additional composition can expelled together (at the same time) or individually. If expelled together, the two compositions can mixed in the hands and the mixture applied to the hair.

Methods of treating hair according to the disclosure may vary but typically include applying a hair-treatment composition of the instant disclosure to the hair (wet, damp, or dry hair), allowing the hair-treatment to remain on the hair for a sufficient amount of time, and rinsing the hair-treatment compositions from the hair. The hair-treatment composition may be applied to the hair in a sequence with other hair-treatment compositions. For example, the hair-treatment compositions may be applied to the hair before shampooing the hair, after shampooing the hair, before conditioning the hair, and/or after conditioning the hair. The hair-treatment compositions, however, are not required to be used in a sequence.

In some case, the hair-treatment compositions are used in conjunction with additional hair-treatment compositions in a routine, for example, during an individual's normal showering/bathing routine. The hair-treatment composition may be applied to the hair individually or may be combined with one or more additional hair-treatment compositions. Combining the hair-treatment compositions with one or more additional hair treatment compositions (e.g., a shampoo, a conditioner, a rinse, etc.) can be useful for eliminating multiple steps from a routine. For instance, the hair-treatment composition may be mixed with a shampoo (or conditioner) prior to application to the hair. In this case, the mixture of the shampoo (or conditioner) and the hair-treatment composition are simultaneously applied to the hair during the cleansing or conditioning process and simultaneously rinsed from the hair. Alternatively, the hair-treatment composition may be layered on top of (or lathered into) hair to which a shampoo (or conditioner) has already been applied or vice versa. In this case, the hair-treatment composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the hair-treatment composition is also applied to the hair.

When used in conjunction with a shampoo and/or a conditioner, the hair-treatment composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair-treatment composition of the instant disclosure: shampoo/conditioner, etc.).

The hair-treatment compositions may be allowed to remain on the hair for a minimum amount of time before being rinsed from the hair, but allowing the hair-treatment composition to remain on the hair for an extended period of time is not needed. Conveniently, the hair-treatment compositions can be applied and allowed to remain on the hair for a period of time that is typical for regular shampooing and/or conditioning. For example, the hair-treatment composition (whether combined with another hair-treatment composition such as a shampoo or conditioner) may be applied to the hair and allowed to remain on the hair for a few seconds (1, 2, 3, or 5 seconds) up to about 1, about 2, about 5, about 10, about 15, about 20, about 25, or about 30 minutes.

When the hair-treatment composition is not being mixed with another hair treatment composition prior to application to the hair, the hair-treatment composition may be applied to the hair immediately after or before the hair it treated with another hair treatment composition (e.g., a shampoo and/or a conditioner). For example, the hair-treatment compositions may be applied to the hair within about 1, 2, 5, 10, or 20 minutes before or after a shampoo and/or a conditioner is applied to the hair.

Finally, as mentioned previously, the hair-treatment compositions are unique in their ability to provide hair with improved manageability, long-lasting style and frizz control, and protection. Accordingly, the instant disclosure relates to methods for treating hair, for example, for improving the manageability of hair, for imparting lasting style and frizz control, and for protecting the hair from damage, especially heat damage. More specifically, the hair-treatment compositions may be used in methods for conditioning the hair, providing curl definition to the hair, providing frizz control to the hair, improving ease of combability and detangling, protecting the hair from damage, including heat damage, and increasing the appearance of hair volume.

More exhaustive but non-limiting lists of components useful in the hair-treatment compositions disclosed herein are provided below.

Polyurethane Latex Polymers

Polyurethane latex polymers that be used in the instant hair-treatment compositions include, polyurethane latex polymers such as aqueous polyurethane dispersions comprising the reaction products of (i), (ii), and/or (iii), defined below.

Reaction product (i) may be any prepolymer according to the formula:

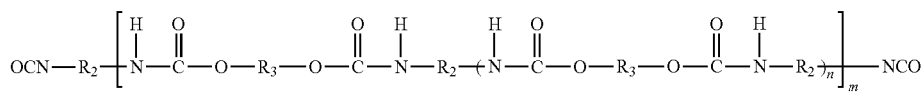

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecane-dioic, 1,3-cyclohexanedicarboxylic, 1,4-cyclo-hexane-dicarboxylic, 2,5-norboranedicarboxylic, diglycolic, thiodipropionic, 2,5-naphthalene-dicarboxylic, 2,6-naphthalene-dicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythio-ether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexane-diol. Polyacetals useful according to various non-limiting embodiments of the disclosure can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula R2(NCO)2, in which R2 represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanato-methyl-3,5,5-trimethyl-cyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxy-cyclo-hexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylol-butanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

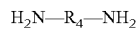

wherein $R_4$ is chosen from alkylene or alkylene oxide radicals, said radicals not being substituted with ionic or potentially ionic groups.

Reaction product (ii) may optionally be chosen from alkylene diamines, such as hydrazine, ethylene-diamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophorone-diamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

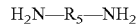

wherein $R_5$ is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, $R_5$ represents an alkylene radical substituted with sulphonic acid or sulphonate groups. By way of example only, the compound is chosen from sodium salts of N-(2-aminoethyl)-2-aminoethanesulphonic acid.

By way of non-limiting example, such polyurethane latex polymers include, but are not limited to, aqueous polyurethane dispersions comprising a reaction product of a prepolymer such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), polycarbonate polyurethane, aliphatic polyurethane and aliphatic polyester polyurethane (such as the NEOREZ® series, DSM, such as NEOREZ® R989, and NEOREZ® R-2202).

Thickening Agents

Thickening agents (also referred to as thickeners or viscosity modifying agents) are well known. Classes of such agents include, but are not limited to, viscous liquids, such as polyethylene glycol, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof.

In some cases, the thickening agents may include one or more associative thickening polymers such as anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof. The associative thickening polymers, for instance, the acrylates copolymer and/or the acrylates crosspolymer-4, may be neutralized in water or an aqueous solution with a neutralizing agent before the polymer is added into a hair-treatment composition. In some cases, associative thickening polymers may be useful in anionic surfactant-free hair-treatment compositions, in particular, anionic surfactant free conditioning shampoos. For example, the anionic surfactant-free conditioning shampoos may include one or more anionic associative polymers.

Water-Soluble Solvents

The term "water-soluble solvent" is interchangeable with the term "water-miscible solvent" and means a compound that is liquid at 25° C. and at atmospheric pressure (760 mmHg), and it has a solubility of at least 50% in water under these conditions. The hair-treatment compositions of the instant disclosure may include one or more water-soluble solvents.

Water-soluble solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, propylene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof.

Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

Fatty Compounds

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of glycol distearate, PEG-55 propylene glycol oleate, cetearyl alcohol, soybean oil, cetyl esters, isononanoate isopropyl myristate, cetearyl alcohol, orbigynya oleifera seed oil, propylene glycol dicaprylate/dicaprate, mineral oil, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcocohl, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

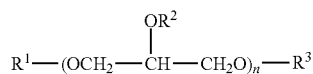

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

Silicones

Exemplary silicones include, without limitation, cyclic silicones, such as those having 3 to 6, or 3 to 4 or 3 to 5, (or any of 3, 4, 5, or 6) Si—O groups in the cyclic backbone chain (e.g., siloxanes). In some cases, the cyclic silicone is a volatile silicone. In some cases, the cyclic silicone is a low viscosity silicone. Exemplary cyclic silicones include, without limitation, cyclomethicone, cyclotetrasiloxane, cyclopentasiloxane (e.g., Cyclomethicone 5-NF), cyclohexasiloxane and a mixture of cyclohexasiloxane and cyclopenasiloxane (e.g., DOW CORNING 246 Fluid (d6+d5)). Other non-limiting examples of silicones are silicones having side groups or side chains. In some cases, the side groups are hydrophobic. In some cases, the side groups are straight chained, while in other embodiments the side groups are branched. Exemplary side chains include those having 1 to 6, or 2 to 6, or 3 to 6 or 3 to 6 or 5 to 6 carbons or heteroatoms (e.g., O, S, or N) (or a mixture thereof). Exemplary linear side chains include, without limitation, methyl, ethyl, propyl, butyl, pentyl, and hexyl. Exemplary branched side chains include, without limitation, isopropyl, isobutyl, and tert-butyl. In one nonlimiting embodiment, the branched side chain is —O—Si(CH$_3$)$_3$. Nonlimiting examples of silicones having branched side chains are stearyl dimethicone and phyenyltrimethicone, cetyl dimethicone, caprylyl methicone, PEG/PPG 18/18 dimethicone the structures of which are as follows:

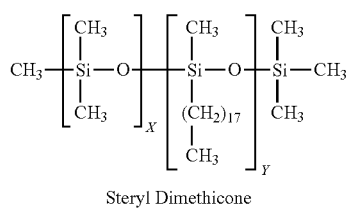

Steryl Dimethicone

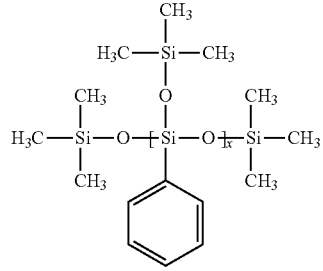

Phenyltrimethicone

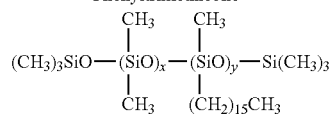

Cetyl Dimethicone

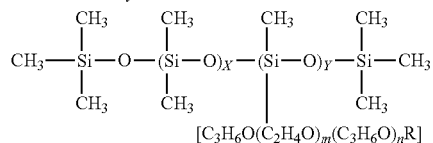

PEG/PPG 18/18 dimethicone

In the above formulas m, n, x, and y may independently be integers of 1 to 100, 1 to 80, 1 to 60, 1 to 50, 1 to 40, 1 to 30, 1 to 20, or 1 to 10. In some cases, the side chains are cyclic. Cyclic side chains include aliphatic side chains and aromatic side chains. A nonlimiting example of a cyclic side chain is phenyl.

With regard to silicones having hydrophilic or polar groups, as described previously, silicones that are repulsive with regard to the hydrophobic chains of the oil are thought to produce more stable foams because they do not inhibit the hydrophobic-hydrophobic interactions of the oil. Exemplary hydrophilic or polar groups include oxygen-containing groups, such as carbonyl groups, hydroxy groups, ether, ester, carboxylic groups, which replace one or more methyl groups. The hydrophilic/polar groups are present alternatively in the main chain of the silicone or in a side chain. Nonlimiting examples of a silicone having a hydrophilic group are PEG/PPG 18/18 dimethicone and dimethiconol, the structures of which are:

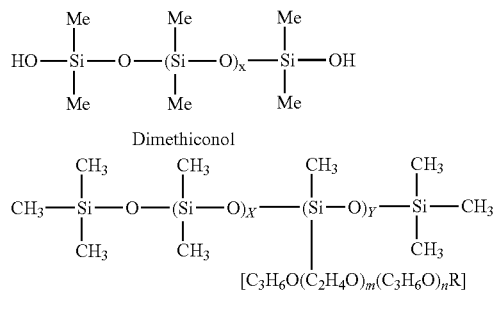

PEG/PEG 18/18 Dimethicone

X, y, m, and n are as defined above, and R is a C$_1$ to C$_{10}$ alkyl.

Another type of specific non limiting volatile silicone is a volatile short chain linear alkylmethylsilicone fluid. The volatile short chain linear alkylmethylsilicone fluid has the formula:

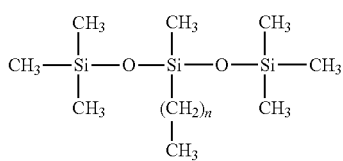

In the above formula, the integer represented by n has a value of five to twelve. Preferably, n has a value of five to eight. Compounds include, for example, 3-hexyl-1,1,1,3,5,5-heptamethyltrisiloxane and 3-octyl-, 1,1,3,5,5,5-heptamethyltrisiloxane.

Yet another type of volatile silicone in accordance with the present invention is a volatile short chain linear phenylmethylsilicone fluid. The volatile short chain linear phenylmethylsilicone fluid has the formula:

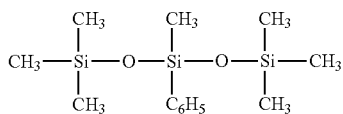

This compound is 3-phenyl-1,1,1,3,4,4,4-heptamethyltrisiloxane. Further volatile silicone fluids useful in the compositions described herein include, without limitation, are decamethylcyclopentasiloxane (DMCPS) which has a molecular weight of about 370, a refractive index of 1.40, and the formula [(Me$_2$)SiO]$_5$; the compound 3-hexyl-1,1,1,3,5,5,5-heptamethyltrisiloxane (HHMTS) which has a molecular weight of about 306, and a refractive index of 1.41; and the compound 3-phenyl-1,1,1,3,5,5,5-heptamethyltrisiloxane (PHMTS) which has a molecular weight of about 298 and a refractive index of 1.45.

As amino silicone that may be used in the scope of the instant disclosure, the following can be cited:

a) polysiloxanes corresponding to formula (A):

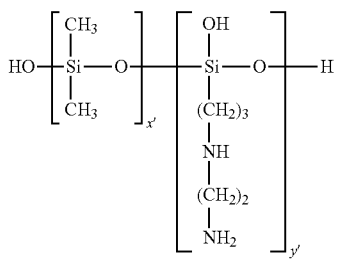

in which x' and y' are integers such that the weight-average molecular weight (Mw) is comprised between about 5000 and 500 000 b) amino silicones corresponding to formula (B):

R'$_a$G$_{3-a}$-Si(OSiG$_2$)n-(OSiGbR'$_{2-b}$)m-O—SiG$_{3-a}$-R'$_a$ (B)

in which:

G, which may be identical or different, designate a hydrogen atom, or a phenyl, OH or C$_1$-C$_8$ alkyl group, for example methyl, or C$_1$-C$_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula —C$_q$H$_{2q}$L in which q is a number ranging from 2 to 8 and L is an optionally quaternized amino group chosen from the following groups:

NR"-Q-N(R")$_2$
N(R")$_2$
N+(R")$_3$A-
N+H(R")$_2$A-
N+H$_2$(R")A-
N(R")-Q-N+R"H$_2$A-
NR"-Q-N+(R")$_2$HA-
NR"-Q-N+(R")$_3$A-, in which R", which may be identical or different, denote hydrogen, phenyl, benzyl, or a saturated monovalent hydrocarbon-based radical, for example a C$_1$-C$_{20}$ alkyl radical; Q denotes a linear or branched CrH$_{2r}$ group, r being an integer ranging from 2 to 6, preferably from 2 to 4; and A- represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

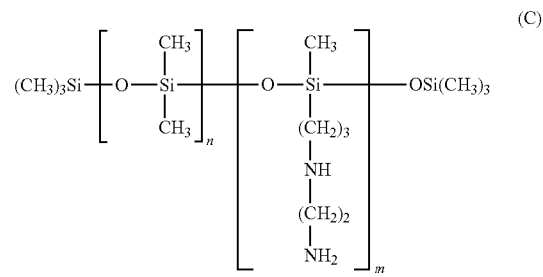

in which n and m have the meanings given above, in formula B.

Another group of amino silicones corresponding to this definition is represented by silicones having the following formulae (D) or (E):

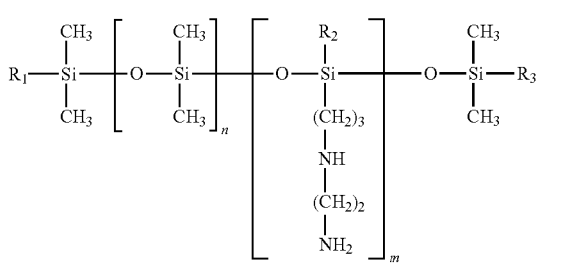

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

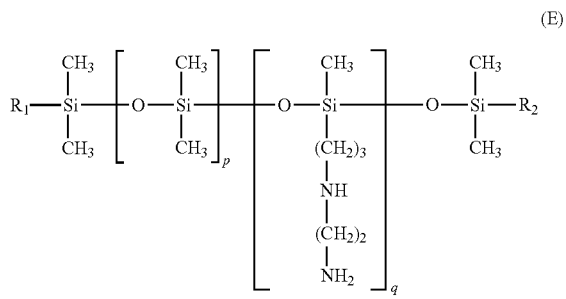

(E)

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300@.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

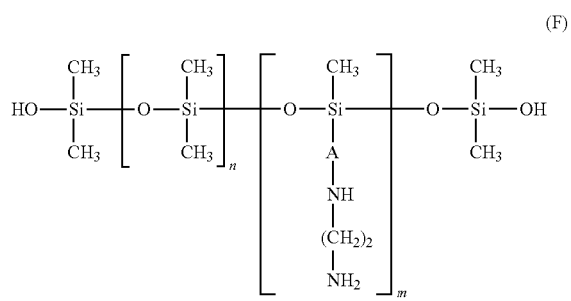

(F)

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

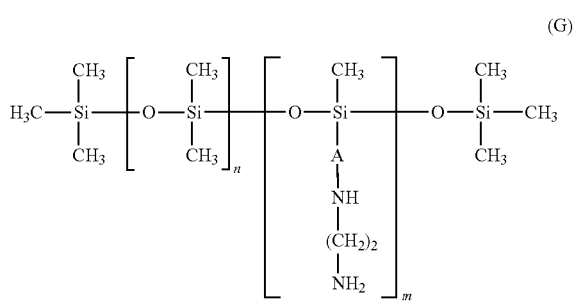

(G)

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

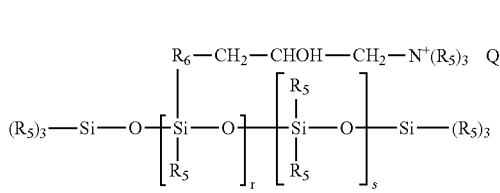

in which:
- $R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- Q- is an anion such as a halide ion, in particular chloride, or an organic acid salt (for example acetate);
- r represents a mean statistical value from 2 to 20 and in particular from 2 to 8;
- s represents a mean statistical value from 20 to 200 and in particular from 20 to 50.

Such amino silicones are described more particularly in U.S. Pat. No. 4,185,087.

d) quaternary ammonium silicones having formula (I):

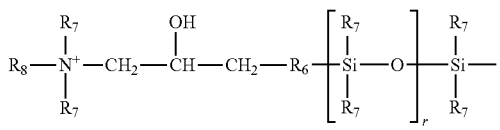

in which:
- $R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- S $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—$NHCOR_7$ radical;
- X— is an anion such as a halide ion, in particular chloride, or an organic acid salt (for example acetate);
- r represents a mean statistical value from 2 to 200 and in particular from 5 to 100;

These silicones are described, for example, in patent application EP-A 0 530 974.

e) amino silicones having formula (J):

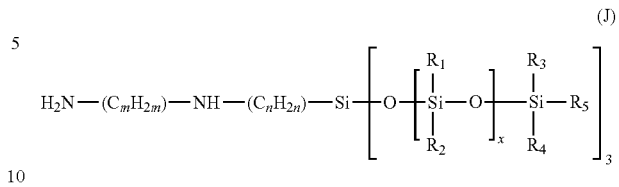

in which:
- $R_1$, $R_2$, $R_3$ and $R_4$, which may be identical or different, denote a $C_1$-$C_4$ alkyl radical or a phenyl group;
- $R_5$ denotes a $C_1$-$C_4$ alkyl radical or a hydroxyl group;
- n is an integer ranging from 1 to 5;
- m is an integer ranging from 1 to 5;
- and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

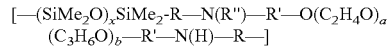

or alternatively

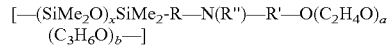

in which:
- a is an integer greater than or equal to 1, preferably ranging from 5 to 200, more particularly ranging from 10 to 100;
- b is an integer comprised between 0 and 200, preferably ranging from 4 to 100, more particularly between from 5 and 30;
- x is an integer ranging from 1 to 10 000, more particularly from 10 to 5000;
- R" is a hydrogen atom or a methyl;
- R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;
- R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names Silsoft™ A-843 or Silsoft™ A+ by Momentive.

g) the alkylamino silicones corresponding to formula (K) below:

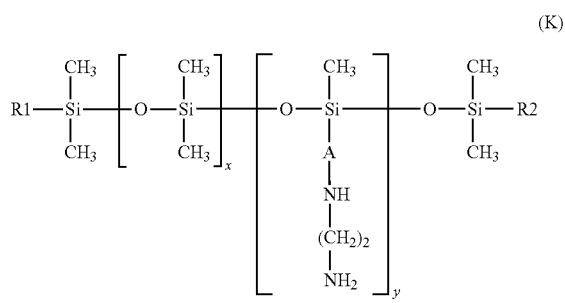

(K)

in which:
x and y are numbers ranging from 1 to 5000; preferably, x ranges from 10 to 2000 and especially from 100 to 1000; preferably, y ranges from 1 to 100;
$R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;
A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —$CH_2CH_2CH_2$— and —$CH_2CH(CH_3)CH_2$—.

Preferably, $R_1$ and $R_2$, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, $R_1$ and $R_2$, which may be identical or different, are chosen from hexadecyl (cetyl) and octadecyl (stearyl) radicals.

Preferentially, the silicone is of formula (K) with:
x ranging from 10 to 2000 and especially from 100 to 1000;
y ranging from 1 to 100;
A comprising 3 to 6 carbon atoms and especially 4 carbon atoms;
preferably, A is branched; and more particularly A is chosen from the following divalent radicals: $CH_2CH_2CH_2$ and —$CH_2CH(CH_3)CH_2$—; and
$R_1$ and $R_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

Useable silicones also include silicone-organic polymer hybrid compounds, for example, silicone polyvinyl acetate compounds. The silicone-organic polymer hybrid compounds may also be chosen from a cross-linked anionic copolymer comprised of organic polymer blocks and silicone blocks, resulting in a multiblock polymer structure.

The silicone-organic polymer hybrid compounds may be cross-linked anionic copolymers comprising at least one cross-linked polysiloxane structural unit. Examples of these polymers are described in PCT publication WO2011069786, which is incorporated herein by reference in its entirety.

Emulsifiers

The emulsifiers are appropriately chosen according to the emulsion to be obtained (W/O or O/W). Non-limiting examples of emulsifiers may include esters of polyols and of a fatty acid having an alkyl chain containing from 12 to 22 carbon atoms, such as esters of fatty acid and of glycerol, of glucose or of sorbitol; oxyethylenated derivatives of esters of polyols and of a fatty acid having an alkyl chain containing from 12 to 22 carbon atoms, which derivatives contain from 1 to 50 oxyethylene groups, such as a complex of triisostearin (triester of glycerol and of isostearic acid) and of PEG-6; ethers of polyethylene glycol and of a fatty alcohol having an alkyl chain containing from 12 to 22 carbon atoms, which ethers contain from 1 to 50 oxyethylene groups, such as oleyl ethers and in particular oleth-25 (25 oxyethylene groups), and their mixtures.

Also included are polyol fatty esters and fatty ethers with a branched or unsaturated chain containing from 12 to 22 carbon atoms and, in particular, sorbitan monoisostearate, such as the product sold under the name "Arlacel 987" by the company ICI, sorbitan mono/dioleate, such as the product sold under the name "Arlacel 83" by the company ICI, the complex of triisostearin and of PEG-6, such as the product sold under the name "Labrafil isostearic" by the company Gattefosse, decaglyceryl pentaisostearate, such as the product sold under the name "Nikkol Decaglyn 5-IS" by the company Nikko Chemical, or methyl glucose dioleate, such as the product sold under the name "Isolan DO" by the company Goldschmidt.

Other examples of emulsifiers include esters of polyethylene glycol and of a fatty acid having an alkyl chain containing from 12 to 22 carbon atoms, which esters contain from 5 to 100 and preferably from 20 to 60 oxyethylene groups, such as PEG-40 stearate; ethers of polyethylene glycol and of a fatty alcohol having an alkyl chain containing from 12 to 22 carbon atoms, which ethers contain from 5 to 100 and preferably from 10 to oxyethylene groups, such as ceteareth-25 or ceteth-25; esters of sorbitan and of a fatty acid having an alkyl chain containing from 12 to 22 carbon atoms, which esters comprise from 0 to 100 and preferably from 4 to 25 oxyethylene groups, such as polysorbate 20, polysorbate 40 and polysorbate 60; esters of sugar and of a fatty acid having an alkyl chain containing from 12 to 22 carbon atoms, such as sucrose stearate; derivatives of polyethylene glycol and of esters of glycerol and of a fatty acid having an alkyl chain containing from 12 to 22 carbon atoms, such as PEG-8 caprylic/capric glycerides; polyethylene glycol ethers of esters of methyl glucose and of a fatty acid having an alkyl chain containing from 12 to 22 carbon atoms, such as PEG-20 methyl glucose sesquistearate; and their mixtures.

Suitable emulsifiers may be chosen from glyceryl esters and polyethylene glycol esters of stearic acid, such as glyceryl stearate and PEG-100 stearate.

The emulsifier may also be chosen from alkylpolyglycosides, including those having with an HLB of less than 7. For example, alkylpolyglycosides include those of the following formula:

in which R represents a branched and/or unsaturated alkyl radical comprising from 14 to 24 carbon atoms, G represents a reduced sugar comprising 5 or 6 carbon atoms, and x is a value ranging from 1 to 10, from 1 to 4, and G especially denotes glucose, xylose, fructose, or galactose. The unsaturated alkyl radical may comprise one or more ethylenic unsaturations, and in particular one or two ethylenic unsaturations.

As alkylpolyglycosides of this type, mention may be made of alkylpolyglucosides (G=glucose or xylose), and especially the compounds in which R represents an olelyl radical (unsaturated C18 radical) or isostearyl (saturated C18 radical) or a octyldodecyl (C20), G denotes glucose or xylose, x is a value ranging from 1 to 2, especially isostearyl glucoside, oleyl glucoside, octyldodecyl xyloside, and mixtures thereof. This alkylpolyglucoside may be used as a mixture with a coemulsifier, more especially with a fatty alcohol or a fatty acid (fatty compounds according to the instant disclosure), and especially a fatty alcohols or fatty acids containing the same fatty chain as that of the alkylpolyglucoside, i.e. comprising from 14 to 24 carbon atoms and containing a branched and/or unsaturated chain, for example isostearyl alcohol when the alkylpolyglucoside is isostearyl glucoside, and oleyl alcohol when the alkylpolyglucoside is oleyl glucoside, and octyldodecanol when the alkylpolyglucoside is octyldodecyl xyloside, optionally in the form of a self-emulsifying composition, as described, for example, in document WO-A-92/06778, which is incorporated herein by reference in its entirety. Use may be made, for example, of the mixture of isostearyl glucoside and isostearyl alcohol, sold under the name MONTANOV WO 18 by the company SEPPIC, and also the mixture octyldodecanol and octyldodecyl xyloside sold under the name FLUDANOV 20 by the company SEPPIC.

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name DOW CORNING 5200 Formulation Aid by the company Dow Corning; cetyldimethicone copolyol, such as the product sold under the name ABIL EM 90R by the company Evonik, and the mixture of cetyldimethicone copolyol, of polyglyceryl isostearate (4 mol) and of hexyl laurate, sold under the name ABIL WE 09 by the company Evonik. One or more co-emulsifiers may also be added thereto, which may be chosen advantageously from the group comprising polyol alkyl esters.

Polyol alkyl esters that may especially be mentioned include polyethylene glycol esters, for instance PEG-30 dipolyhydroxystearate, such as the product sold under the name ARLACEL P135 by the company Croda.

Glycerol and/or sorbitan esters that may be mentioned include, for example, polyglyceryl isostearate, such as the product sold under the name ISOLAN GI 34 by the company Evonik, sorbitan isostearate, such as the product sold under the name ARLACEL 987 by the company Croda, sorbitan glyceryl isostearate, such as the product sold under the name ARLACEL 986 by the company Croda, and mixtures thereof.

Emulsifying polyoxyalkylenated silicone elastomers may especially be also mentioned as those disclosed in the documents U.S. Pat. Nos. 5,236,986, 5,412,004, 5,837,793, 5,811,487, which are all incorporated herein by reference in their entirety. As examples of polyoxyethylenated silicone elastomers, mention is made of those sold by the company Shin Etsu, with the denominations: KSG-21 (at 27% in active material) INCI name: Dimethicone/PEG-10 Dimethicone vinyl dimethicone crosspolymer), KSG-20 (at 95% % in active material) INCI name: PEG-10 Dimethicone Crosspolymer), KSG-30, (at 100% % in active material) INCI name: Lauryl PEG-15 Dimethicone vinyl dimethicone crosspolymer), KSG-31 (at 25% % in active material) INCI name: Lauryl PEG-15 Dimethicone vinyl dimethicone crosspolymer), KSG-32 or KSG-42 or KSG-320 ou KSG-30 (at 25% % in active material) INCI name: Lauryl PEG-15 Dimethicone vinyl dimethicone crosspolymer), KSG-33 (at 20% in active material), KSG-210 (at 25% % in active material) INCI name: Dimethicone/PEG-10/15 crosspolymer), KSG-310: lauryl modified polydimethylsiloxane polyoxyethylenated in mineral oil, KSG-330KSG-340, X-226146 (at 32% % in active material) INCI name: Dimethicone/PEG-10 Dimethicone vinyl dimethicone crosspolymer, or those sold by the company Dow Corning under the commercial names: DC9010 (at 9% % in active material) INCI name: PEG-12 dimethicone crosspolymer) DC9011 at 11% % in active material.

Amongst water/oil emulsifiers, mention is made of polyglycerolated silicone elastomers. Non-limiting examples of polyglycerolated silicone elastomers include those sold by the company Shin Etsu, with the denominations: KSG-710, (at 25% in active material (INCI name: Dimethicone/Polyglycerin-3 Crosspolymer).

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate sold, for example, by the company Croda under the name ARLACEL 165; oxyalkylenated (oxyethylenated and/or oxypropylenated) fatty alkyl ethers; sugar esters, for instance sucrose stearate; fatty alkyl ethers of sugars, especially alkyl polyglucosides (APG) such as decylglucoside and laurylglucoside sold, for example, by the company Cognis under the respective names PLANTAREN 2000 and PLANTAREN 1200, cetostearyl glucoside optionally as a mixture with cetostearyl alcohol, sold, for example, under the name MONTANOV 68 by the company SEPPIC, under the name TEGOCARE CG90 by the company Evonik and under the name EMULGADE KE3302 by the company Cognis, and also arachidyl glucoside, for example in the form of a mixture of arachidyl alcohol, behenyl alcohol and arachidyl glucoside, sold under the name MONTANOV 202 by the company SEPPIC. According to a specific embodiment of the invention, the mixture of the alkyl polyglucoside as defined above with the corresponding fatty alcohol can be in the form of a self-emulsifying composition, for example as disclosed in the document WO-A-92/06778; the hydrophobically modified inulines as Inuline Lauryl Carbamate as the product sold under the denomination INUTEC SP1 by the Company Beneo-ORAFTI.

In some cases, the hair-treatment composition may include an emulsifier such as dimers surfactants named "gemini surfactants" and comprising two surfactant moieties identical or different, and constituted by an hydrophilic head group and a lipophilic group linked to each other through the head groups, thanks to a spacer. One can use for example a gemini surfactant such as those sold by Sasol company under the name CERALUTIOM, for example, CERALUTION H: Behenyl Alcohol, Glyceryl Stearate, Glyceryl Stearate Citrate et Sodium Dicocoyl ethylenediamine PEG-15 Sulfate, CERALUTION F: Sodium Lauroyl Lactylate et Sodium Dicocoyl ethylenediamine PEG-15 Sulfate, CERALUTION C: Aqua, Capric/Caprylic triglyceride, Glycerine, Ceteareth-25, Sodium Dicocoyl ethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben. Among other emulsifiers, amphiphilic copolymers of 2-acrylamido 2-methylpropane sulfonic acid may be used. Non-limiting examples of AMPS copolymers include ammonium acryloyldimethyltaurate/steareth-25 methacrylate crosspolymer sold under the name ARISTOFLEX HMS by the Company Clariant, ammonium acryloyldimethyltaurate/steareth-8 methacrylate copolymer sold under the name ARISTOFLEX SNC by the company Clariant.

Amphoteric Surfactants

Amphoteric surfactants useful in the cosmetic compositions disclosed herein may be chosen from betaines, sultaines, amphoacetates, amphoproprionates, and a mixture thereof. More typically, betaines and amphoproprionates are used, and most typically betaines. Betaines which can be used in the current compositions include those having the formulas below:

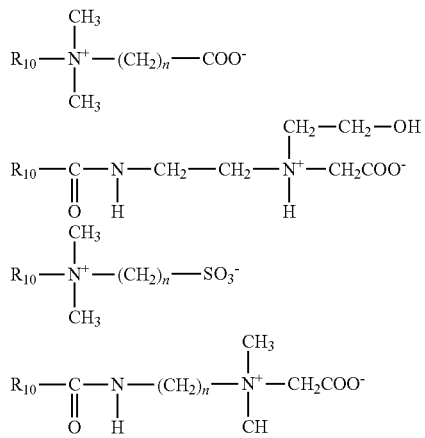

wherein
$R^{10}$ is an alkyl group having 8-18 carbon atoms; and
n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and a mixture thereof. Typically, the at least one betaine compound is selected from the group consisting of coco betaine, cocoamidopropyl betaine, behenyl betaine, capryl/capramidopropyl betaine, lauryl betaine, and a mixture thereof, and more typically coco betaine and/or cocoamidopropyl betaine.

Hydroxyl sultaines useful in the compositions of the invention include the following

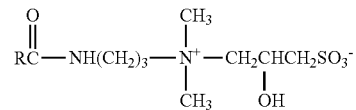

wherein
R is an alkyl group having 8-18 carbon atoms.
Useful alkylamphoacetates include those having the formula

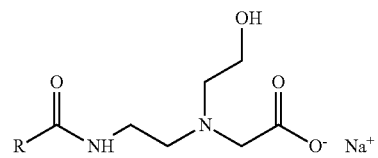

wherein
R is an alkyl group having 8-18 carbon atoms.
useful alkyl amphodiacetates include those having the formula

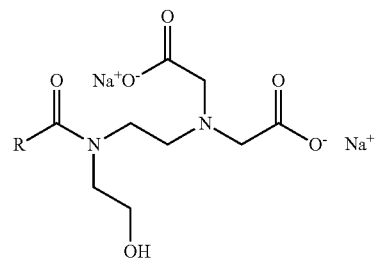

wherein
R is an alkyl group having 8-18 carbon atoms.
The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of $(C_5\text{-}C_{20})$alkylbetaines, $(C_5\text{-}C_{20})$alkylamido $(C_1\text{-}C_6)$alkylbetaines, sulfobetaines, $(C_5\text{-}C_{20})$alkylsulfobetaines, $(C_5\text{-}C_{20})$alkylamido $(C_1\text{-}C_6)$alkylsulfobetaines, $(C_5\text{-}C_{20})$alkylamphoacetate, $(C_5\text{-}C_{20})$alkylamphodiacetate, and a mixture thereof.

Among the optionally quaternized secondary or tertiary aliphatic amine derivatives that may be used, mention may also be made of the products of respective structures (A1) and (A2) below:

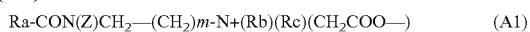

Ra-CON(Z)CH$_2$—(CH$_2$)$_m$-N+(Rb)(Rc)(CH$_2$COO—)   (A1)

in which:
Ra represents a $C_{10}$-$C_{30}$ alkyl or alkenyl group derived from an acid Ra—COOH preferably present in hydrolysed coconut oil, a heptyl group, a nonyl group or an undecyl group, Rb represents a p-hydroxyethyl group,
Rc represents a carboxymethyl group;
m is equal to 0, 1 or 2,
Z represents a hydrogen atom or a hydroxyethyl or carboxymethyl group;

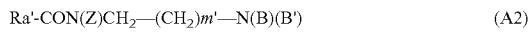
$$Ra'\text{-}CON(Z)CH_2\text{—}(CH_2)m'\text{—}N(B)(B') \quad (A2)$$

in which:
B represents —CH$_2$CH$_2$OX', with X' representing —CH$_2$—COOH, CH$_2$—COOZ', CH$_2$CH$_2$—COOH, —CH$_2$CH$_2$—COOZ', or a hydrogen atom,
B' represents —(CH$_2$)z-Y', with z=1 or 2, and Y' representing COOH, COOZ', CH$_2$—CHOH—SO$_3$H or —CH$_2$—CHOH—SO$_3$Z',
m' is equal to 0, 1 or 2,
Z represents a hydrogen atom or a hydroxyethyl or carboxymethyl group,
Z' represents an ion resulting from an alkali or alkaline-earth metal, such as sodium, potassium or magnesium; an ammonium ion; or an ion resulting from an organic amine and in particular from an amino alcohol, such as monoethanola-mine, diethanolamine and triethanolamine, monoisopropanolamine, diisopropa-nolamine or triisopropanolamine, 2-amino-2-methyl-1-propanol, 2-amino-2-methyl-1,3-propanediol and tris(hydroxymethyl) aminomethane,
Ra' represents a C$_{10}$-C$_{30}$ alkyl or alkenyl group of an acid Ra'COOH preferably pre-sent in hydrolysed linseed oil or coconut oil, an alkyl group, in particular a C$_{17}$ alkyl group, and its iso form, or an unsaturated C$_{17}$ group.

Among the compounds corresponding to formula (A2) in which X' represents an hydrogen atom, mention may be made of compounds under the names sodium cocoamphoacetate, sodium lauroamphoacetate, sodium caproamphoacetate and sodium capryloamphoacetate.

Other compounds corresponding to formula (A2) are disodium cocoamphodiacetate, disodium lauroamphodiacetate, disodium caproamphodiacetate, disodium capryloamphodiacetate, disodium cocoamphodipropionate, disodium lauroam-phodipropionate, disodium caproamphodipropionate, disodium capryloamphodi-propionate, lauroamphodi-propionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (A3):

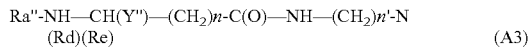
$$Ra''\text{-}NH\text{—}CH(Y'')\text{—}(CH_2)n\text{-}C(O)\text{—}NH\text{—}(CH_2)n'\text{-}N(Rd)(Re) \quad (A3)$$

in which:
Ra" represents a C10-C30 alkyl or alkenyl group of an acid Ra"'—C(O)OH preferably present in hydrolysed linseed oil or coconut oil;
Y" represents the group —C(O)OH, —C(O)OZ", —CH$_2$—CH(OH)—SO$_3$H or the group CH$_2$—CH(OH)—SO$_3$—Z", with Z" representing a cationic counterion resulting from an alkali metal or alkaline-earth metal, such as sodium, an ammonium ion or an ion resulting from an organic amine;
Rd and Re represent, independently of each other, a C$_1$-C$_4$ alkyl or hydroxyalkyl radical; and
n and n' denote, independently of each other, an integer ranging from 1 to 3.

Among the compounds corresponding to formula (A3), mention may in particular be made of the compound under the name sodium diethylaminopropylcocoaspartamide.

Preferably, the amphoteric surfactants are chosen from (C$_5$-C$_{20}$)alkylbetaines, (C$_8$-C$_{20}$)alkylamido(C$_1$-C$_6$)alkylbetaines, (C$_8$-C$_{20}$)alkylamphoacetates and (C$_8$-C$_{20}$)alkylamphodiacetates, and a mixture thereof.

In some cases, the at least one amphoteric surfactant is chosen from (C$_8$-C$_{20}$)alkyl betaines, (C$_8$-C$_{20}$)alkylamido(C$_1$-C$_6$)alkylbetaines, (C$_8$-C$_{20}$)alkylamphoacetate, (C$_8$-C$_{20}$) alkylamphodiacetate, and their salts, and a mixture thereof. In some cases, the at least one amphoteric surfactant is selected from coco-betaine, cocamidopropylbetaine, sodium cocoamphoacetate, disodium cocoamphodiacetate, and a mixture thereof.

Cationic Polymers

Non-limiting examples of cationic polymers include poly (methacryloyloxyethyl trimethylammonium chloride), polyquaternium-37, quaternized cellulose derivatives, polyquaternium-4, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In some instances, the one or more cationic polymers may be selected from the group consisting of polyquaternium-4, polyquaternium-10, cationic guar derivatives, and a mixture thereof.

The cationic polymers can be a monoalkyl quaternary amine, such as stearyltrimonium chloride, soyatrimonium chloride or coco-ethyldimonium ethosulfate. Other suitable cationic polymers include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic polymers may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic polymers are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryoloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic polymers are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 is sold under the trademark MERQUAT-100, and is described as having a weight average molecular weight of approximately 100,000. A copolymer reaction product of dimethyldiallylammonium chloride with acrylamide monomers is named Polyquaternium-7 is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10. Also useful are quaternized copolymers of hydroxyethylcellulose and dimethyldimethylammonium chloride, having the name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

Implementation of the present disclosure is provided by way of the following examples. The examples serve to illustrate the technology without being limiting in nature.

Example 1

| | (Gels) | | | | | |
|---|---|---|---|---|---|---|
| Component | INCI US | #1 wt. % | #2 wt. % | #3 wt. % | #4 wt. % | #5 wt. % |
| Polyurethane | POLYURETHANE-34 | 1 | 1 | 2 | 1 | 1 |
| Thickening Agents | HYDROXYETHYLCELLULOSE, POLYACRYLAMIDE, HYDROXYPROPYL GUAR, CARBOMER, POTATO STARCH MODIFIED, AND/OR STARCH ACETATE | 0.6 | 0.6 | 1.1 | 2 | 1 |
| Film-Forming Polymers | PVP, ACRYLATES COPOLYMER, AND/OR VP/DIMETHYLAMINO-ETHYLMETHACRYLATE COPOLYMER | 1 | | | 4.9 | 0.6 |

-continued

| | (Gels) | | | | | |
|---|---|---|---|---|---|---|
| Component | INCI US | #1 wt. % | #2 wt. % | #3 wt. % | #4 wt. % | #5 wt. % |
| Cationic Polymer | POLYQUATERNIUM-4 AND/OR POLYQUATERNIUM-11 | | 0.2 | 0.3 | | 0.2 |
| Silicone | PHENYLTRIMETHICONE, DIMETHICONE, PEG/PPG-17/18 DIMETHICONE, DIMETHICONOL, PEG-40/PPG-8 METHYLAMINOPROPYL/ HYDROXYPROPYL DIMETHICONE COPOLYMER, SILICONE QUATERNIUM-16/GLYCIDOXY DIMETHICONE CROSSPOLYMER, AMINOPROPYL PHENYL TRIMETHICONE, AND/OR CROTONIC ACID/VINYL C8-12 ISOALKYL ESTERS/VA/BIS-VINYLDIMETHICONE CROSSPOLYMER | 19 | 19.4 | 7.8 | | 19 |
| Water-Soluble Solvents | GLYCERIN, DIPROPYLENE GLYCOL, PENTYLENE GLYCOL, HEXYLENE GLYCOL, PROPYLENE GLYCOL, AND/OR CAPRYLYL GLYCOL | 48 | 48.4 | 2.8 | 3.2 | 0.1 |
| Humectants (Sugar Alcohols) | HYDROGENATED STARCH HYDROLYSATE | | | | 1.1 | |
| Fatty Compound | C13-16 ISOPARAFFIN AND/OR PEG-40 HYDROGENATED CASTOR OIL | 1.3 | 1.3 | | 0.7 | 0.3 |
| Cationic Surfactants | BEHENTRIMONIUM CHLORIDE AND CETEARYL ALCOHOL (AND) BEHENTRIMONIUM METHOSULFATE | | | 0.4 | | |
| pH Adjuster | OPTIONAL COMPONENT | 0-3 | 0-3 | 0-3 | 0-3 | 0-3 |
| Preservative(s) | OPTIONAL COMPONENT | 0-3 | 0-3 | 0-3 | 0-3 | 0-3 |
| Fragrance(s) | OPTIONAL COMPONENT | 0-3 | 0-3 | 0-3 | 0-3 | 0-3 |
| Water | WATER | Q.S. | Q.S. | Q.S. | Q.S. | Q.S. |

Example 2

| | (Water-In-Oil Emulsions) | | | |
|---|---|---|---|---|
| Component | INCI US | #6 wt. % | #7 wt. % | #8 wt. % |
| Polyurethane | POLYURETHANE-34 | 0.8 | 0.8 | 2.5 |
| Thickening Agent | POLYACRYLAMIDE | 0.8 | 0.8 | 2.5 |
| Film-Forming Polymer | VP/DIMETHYLAMINOETHYLMETHACRYLATE COPOLYMER | | | 9 |
| Emulsifiers | OCTYLDODECYL XYLOSIDE, PEG-30 DIPOLYHYDROXYSTEARATE AND/OR LAURETH-7 | 0.9 | 0.9 | 0.8 |
| Fatty Compound | C13-14 ISOPARAFFIN, ISONONYL ISONONANOATE, HYDROGENATED POLYISOBUTENE, AND/OR OCTYLDODECANOL | 10.6 | 10.6 | 8.2 |
| Water-Soluble Solvent | PROPYLENE GLYCOL | | | 1.5 |
| Humectants (Sugar Alcohols) | HYDROGENATED STARCH HYDROLYSATE, XYLITYL GLUCOSIDE, XYLITOL AND/OR ANHYDROXYLITOL | | 3 | 1.5 |
| pH Adjuster(s) | OPTIONAL COMPONENT | 0-3 | 0-3 | 0-3 |
| Fragrance(s) | OPTIONAL COMPONENT | 0-3 | 0-3 | 0-3 |
| Preservative(s) | OPTIONAL COMPONENT | 0-3 | 0-3 | 0-3 |
| Water | WATER | Q.S. | Q.S. | Q.S. |

Example 3

(Oil-In-Water Emulsion)

| Component | INCI US | #9 wt. % |
|---|---|---|
| Polyurethane | POLYURETHANE-34 | 1 |
| Thickening Agents | HYDROXYPROPYL GUAR AND/OR POTATO STARCH MODIFIED | 0.7 |
| Film-Forming Polymer | PVP | 2.9 |
| Fatty Compounds | BEESWAX, SHEA BUTTER, CETEARYL ALCOHOL AND/OR CETYL ESTERS | 14.3 |
| Emulsifiers | GLYCERYL STEARATE AND/OR CETEARYL GLUCOSIDE | 4.4 |
| Cationic Polymer | POLYQUATERNIUM-11 | 0.2 |
| Silicone | PHENYL TRIMETHICONE | 0.3 |
| Water-Soluble Solvent | GLYCERIN | 2 |
| Fragrance(s) | OPTIONAL COMPONENT | 0-3 |
| Preservative(s) | OPTIONAL COMPONENT | 0-3 |
| Water | WATER | Q.S |

Example 4

(Lotions)

| Component | INCI US | #10 wt. % | #11 wt. % |
|---|---|---|---|
| Polyurethane | POLYURETHANE-34 | 0.8 | 0.8 |
| Thickening Agents | POLYACRYLAMIDE, POTATO STARCH MODIFIED, AND/OR PEG-120 METHYL GLUCOSE TRIOLEATE | 3.2 | 4.0 |
| Amphoteric Surfactant | SODIUM COCOAMPHOPROPIONATE | 12 | 12 |
| Emulsifier | LAURETH-7 | 0.3 | 0.3 |
| Cationic Polymer | POLYQUATERNIUM-11 | | 0.2 |
| Water-Soluble Solvent | PROPYLENE GLYCOL | 1.6 | 1.6 |
| Fatty Compound | C13-14 ISOPARAFFIN | 0.8 | 0.8 |
| Fragrance(s) | OPTIONAL COMPONENT | 0-3 | 0-3 |
| Preservative(s) | OPTIONIAL COMPONENT | 0-3 | 0-3 |
| Water | WATER | Q.S. | Q.S. |

Example 5

Frizz Control Testing with Formulation #1

Testing was carried out to evaluate the frizz of untreated hair tresses (control), tresses treated with Inventive Formulation #1 (Example 1), and tresses treated with a commercial benchmark product. Thirty-six (36) natural wavy brown hair tresses (from IHIP) were shampooed with a pure cleansing shampoo that is commonly used as a control in cosmetic testing. After shampooing, the tresses were allowed to dry overnight in a humidity chamber set at 80% relative humidity. The tresses were then separated into 6 groups of 6 tresses each, and subsequently treated as follows:

Group A: The tresses of Group A were not subsequently treated and were used as the control.

Group B: The tresses of Group B were shampooed with a standard shampoo followed by conditioning with a standard conditioner. The tresses were then blow dried.

Group C: The tresses of Group C were treated with Inventive Formulation #1. Inventive Formulation #1 was allowed to remain on the tresses for 4 minutes before being rinsed from the tresses. The tresses were then blow dried.

Group D: The tresses of Group D were shampooed with a standard shampoo. After rinsing the shampoo from the tresses, Inventive Formulation #1 was applied to the tresses and allowed to remain on the tresses for 4 minutes. After 4 minutes, without rinsing Inventive Formulation #1 from the tresses, a standard conditioner was applied to the tresses (layered onto Inventive Formulation #1), followed by rinsing. The tresses were then blow dried.

Group E: The tresses of Group E were treated with the commercial benchmark product (TRESemme® Leave-In Treatment), which was not rinsed from the hair, per the instructions of the commercial benchmark product. The tresses were then blow dried.

Group F: The tresses of Group F were shampooed with TRESemme® shampoo followed by conditioning with TRESemme® conditioner. After rinsing the conditioner from the hair, the commercial benchmark product (TRESemme® Leave-In Treatment) was applied to the hair. The commercial benchmark product was not rinsed from the hair, per the instructions of the commercial benchmark product. The tresses were then blow dried.

The treatments of Groups A-F described above are summarized in the following table.

| | Pure Cleansing Shampoo | Standard Shampoo | TRESemme® Shampoo | Inventive Formulation #1 | TRESemme Leave-In | Standard Conditioner | TRESemme® Conditioner |
|---|---|---|---|---|---|---|---|
| Group A (Control) | X | X | | | | | |
| Group B (Comparative) | X | X | | | | X | |
| Group C (Inventive) | X | | | X | | | |
| Group D (Inventive) | X | X | | X | | X | |
| Group E (Comparative) | X | X | | | X | | |
| Group F (Comparative) | X | | X | | X* | | X |

*The TRESemme® Leave-In product was applied to the hair after conditioning with TRESemme® conditioner, and was not rinsed from the hair.

After the tresses were dried, initial pictures of each tress were taken before being placed in a humidity chamber set at 80% relative humidity for 72 hours. Tresses were only removed from the chamber to take pictures at 1 hour, 2 hours, 4 hours, 6 hours, 24 hours, 48 hours, and 72 hours. A one way ANOVA test followed by the Holm-Sidak method for multiple comparisons was used to compare the global frizz values of the 5 groups of tresses. If the data failed normality and/or equal variance, the Kruskal-Wallis One Way ANOVA on Ranks test was used. The statistical significance level was set at $p \leq 0.05$. The results for global frizz values ($cm^2$) of the tresses at Initial, 1 hour, 2 hours, 4 hours, 6 hours, 24 hours, 48 hours, and 72 hours is provided in the table below and graphically shown in FIG. 1.

|  | Initial | 1 Hour | 2 Hours | 4 Hours | 6 Hours | 24 Hours | 48 Hours | 72 Hours |
|---|---|---|---|---|---|---|---|---|
| Group A (Control) | 31 | 42 | 47 | 48 | 48 | 51 | 50 | 51 |
| Group B (Comparative) | 35 | 44 | 49 | 52 | 51 | 57 | 52 | 56 |
| Group C (Inventive) | 16 | 23 | 27 | 32 | 32 | 41 | 32 | 33 |
| Group D (Inventive) | 27 | 33 | 39 | 42 | 44 | 45 | 44 | 43 |
| Group E (Comparative) | 33 | 37 | 43 | 46 | 46 | 47 | 47 | 49 |
| Group F (Comparative) | 38 | 56 | 54 | 60 | 60 | 55 | 55 | 58 |

The statistical difference between treatment groups is as follows:

Frizz Initial: A, B, E, F>C

Frizz 1 Hour: A, B, D, E, F>C; F>A, B, D, E

Frizz 2 Hours: A, B, D, E, F>C; F>D

Frizz 4 Hours: A, B, D, E, F>C; F, B>D; F>E, A

Frizz 6 Hours: A, B, D, E, F>C; F>A, D, E

Frizz 24 Hours: B, F>C

Frizz 48 Hours: A, B, D, E, F>C; F>D

Frizz 72 Hours: A, B, E, F>C; B, F>D

The tresses of inventive group C showed the lowest frizz values at each evaluation time followed by those of inventive group D. The tresses of inventive group C showed statistically significant less frizz than the tresses of control group B and comparative group F at all evaluation times. The tresses of inventive group C showed statically significant less frizz than those of comparative group E at initial, 1 hour, 2 hours, 4 hours, 6 hours, 48 hours, and 72 hours. The tresses of inventive group C also showed statistically significant less frizz than those of control group A at all evaluation times except 24 hours. The tresses of inventive group C exhibited a statistically significant less frizz than the tresses of inventive group D at 1 hour, 2 hours, 4 hours, 6 hours, and 48 hours. The tresses of inventive group D showed statistically significant less frizz than those of comparative group F at 1 hour, 2 hours, 4 hours, 6 hours, 48 hours, and 72 hours. The tresses of inventive group D showed statistically significant less frizz than those of control group B at 4 hours and 72 hours.

These results show a statistically significant improvement in frizz (less frizz) when hair is treated with inventive formulation #1 compared to a control and to hair treated with a comparative commercial benchmark product.

Example 6

Frizz Control Testing with Formulation #6

Testing was carried out to evaluate the frizz of untreated hair tresses (control), tresses treated with Inventive Formulation #6 (Example 2), and tresses treated with a commercial benchmark product. Thirty (30) natural wavy brown hair tresses (from IHIP) were shampooed with a pure cleansing shampoo that is commonly used as a control in cosmetic testing. After shampooing, the tresses were allowed to dry overnight in a humidity chamber set at 80% relative humidity. The tresses were then separated into 5 groups of 6 tresses each, and subsequently treated as follows:

Group A: The tresses of Group A were not subsequently treated and were used as the control.

Group B: The tresses of Group B were treated with Inventive Formulation #6. Inventive Formulation #6 was allowed to remain on the tresses for 4 minutes before being rinsed from the tresses. The tresses were then blow dried.

Group C: The tresses of Group C were shampooed with a standard shampoo. After rinsing the shampoo from the tresses, Inventive Formulation #6 was applied to the tresses and allowed to remain on the tresses for 4 minutes. After 4 minutes, without rinsing Inventive Formulation #6 from the tresses, a standard conditioner was applied to the tresses (layered onto Inventive Formulation #6), followed by rinsing. The tresses were then blow dried.

Group D: The tresses of Group D were treated with a commercial benchmark product (John Frieda® 7 Day Volume In-Shower Treatment), which was allowed to remain on the tresses for 4 minutes before being rinsed from the tresses, per the instructions of the commercial benchmark product. The tresses were then blow dried.

Group E: The tresses of Group E were shampooed with John Frieda® shampoo followed by conditioning with John Frieda® conditioner. After the conditioner was rinsed from the tresses, the commercial benchmark product (John Frieda® 7 Day Volume In-Shower Treatment) was applied to the tresses and allowed to remain on the tresses for 4 minutes, followed by rinsing, per the instructions of the commercial benchmark product. The tresses were then blow dried.

The treatments of Groups A-E described above are summarized in the following table.

| | Pure Cleansing Shampoo | Standard Shampoo | John Frieda ® Shampoo | Inventive Formulation #6 | John Frieda In-Shower | Standard Conditioner | John Frieda ® Conditioner |
|---|---|---|---|---|---|---|---|
| Group A (Control) | X | | | | | | |
| Group B (Inventive) | X | | | X | | | |
| Group C (Inventive) | X | X | | X | | X | |
| Group D (Comparative) | X | | | | X | | |
| Group E (Comparative) | X | | X | | X* | | X |

*The John Frida ® In-Shower product was applied to the hair after conditioning with John Frida ® conditioner.

Figure 2:
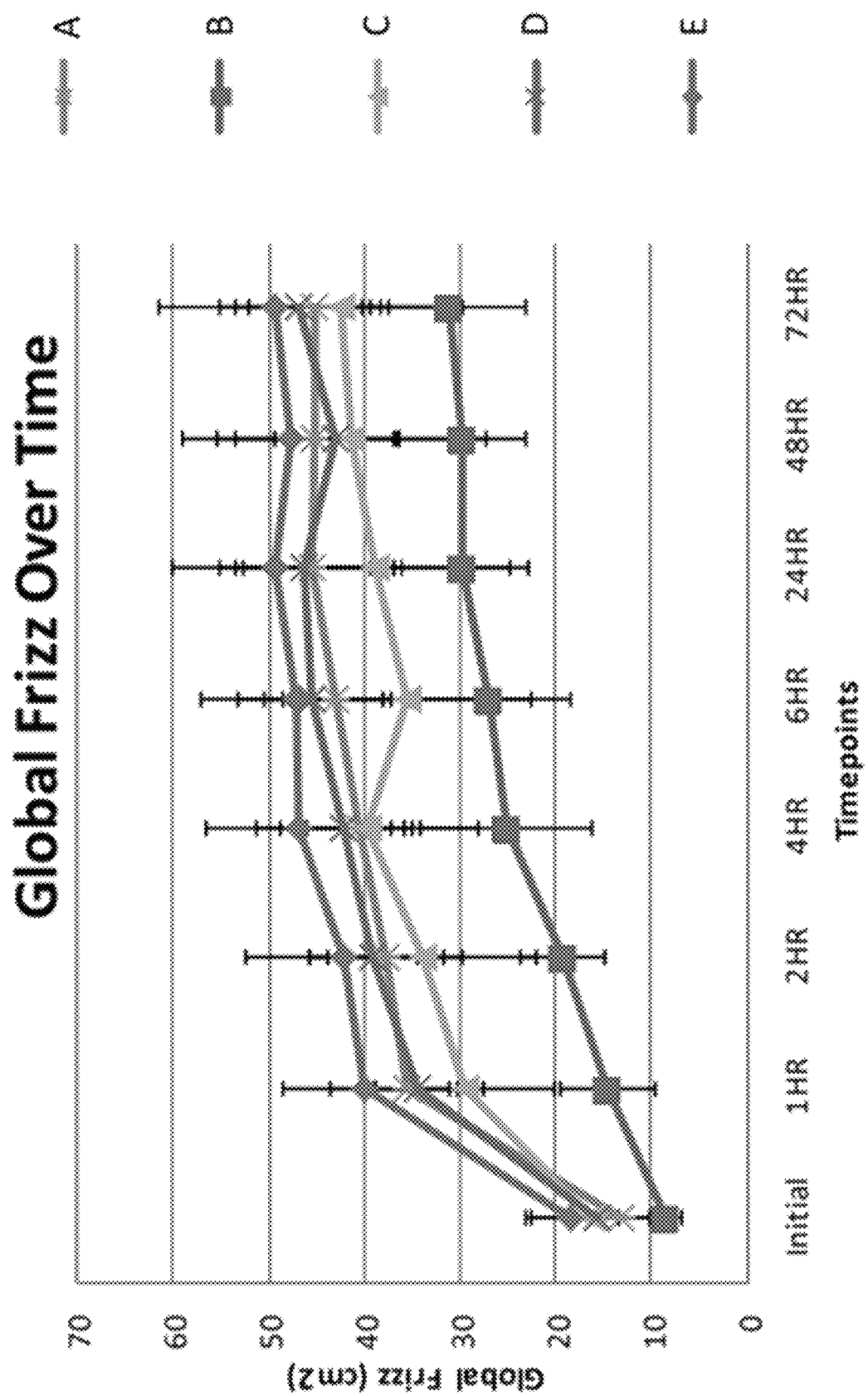
FIG. 2 plots global frizz scores over time for (A) control hair tresses; (B) tresses treated with Inventive Formulation #6; (C) tresses treated with a standard shampoo and standard conditioner in conjunction with Inventive Formulation #6; (D) tresses treated with a commercial benchmark product; and (E) tresses treated with a commercial shampoo and commercial conditioner in conjunction with a commercial benchmark product.

After the tresses were dried, initial pictures of each tress were taken before being placed in a humidity chamber set at 80% relative humidity for 72 hours. Tresses were only removed from the chamber to take pictures at 1 hour, 2 hours, 4 hours, 6 hours, 24 hours, 48 hours, and 72 hours. A one way ANOVA test followed by the Holm-Sidak method for multiple comparisons was used to compare the global frizz values of the 5 groups of tresses. If the data failed normality and/or equal variance, the Kruskal-Wallis One Way ANOVA on Ranks test was used. The statistical significance level was set at $p \leq 0.05$. The results for global frizz values ($cm^2$) of the tresses at Initial, 1 hour, 2 hours, 4 hours, 6 hours, 24 hours, 48 hours, and 72 hours is provided in the table below and graphically shown in FIG. 2.

| | Initial | 1 Hour | 2 Hours | 4 Hours | 6 Hours | 24 Hours | 48 Hours | 72 Hours |
|---|---|---|---|---|---|---|---|---|
| Group A (Control) | 13 | 36 | 38 | 40 | 43 | 45 | 45 | 45 |
| Group B (Inventive) | 8 | 15 | 19 | 25 | 27 | 30 | 30 | 31 |
| Group C (Inventive) | 16 | 29 | 34 | 40 | 36 | 39 | 41 | 42 |
| Group D (Comparative) | 16 | 35 | 39 | 42 | 46 | 46 | 43 | 47 |
| Group E (Comparative) | 18 | 40 | 42 | 47 | 47 | 49 | 48 | 50 |

The statistical difference between treatment groups is as follows:

Frizz Initial: E>B

Frizz 1 Hour: A, C, D, E, >B

Frizz 2 Hours: A, D, E>B

Frizz 4 Hours: D, E>B

Frizz 6 Hours: D, E>B

Frizz 24 Hours: E>B

Frizz 48 Hours: No statistically significant differences

Frizz 72 Hours: E>B

The tresses of inventive group B exhibited statistically significant less frizz than those of comparative groups D and E at 1 hour, 2 hours, 4 hours, and 6 hours. The tresses of inventive group B also exhibited statistically significant less frizz than those of comparative group E at initial, 24 hours and 72 hours. Finally, the tresses of inventive group B exhibited statistically significant less frizz than those of group A (control) at 1 hour and 2 hours.

These results show a statistically significant improvement in frizz (less frizz) when hair is treated with inventive formulation #6 compared to a control and to hair treated with a comparative commercial benchmark product.

Example 7

Wet Combing Testing with Formulation #1

Testing was carried out to determine the wet combing properties of untreated hair tresses (control), tresses treated with Inventive Formulation #1 (Example 1), and tresses treated with a commercial benchmark product (TRE-Semme® Leave-In Product). Forty (40) natural wavy brown hair tresses (from IHIP) were separated into 8 groups of 6 tresses each, and treated as follows:

Group A: The tresses of Group A were shampooed with a standard shampoo and then conditioned with a standard conditioner. The tresses were then blow dried.

Group B: The tresses of Group B were shampooed with a standard shampoo and then conditioned with a standard conditioner. The tresses were blow dried and then styled with a flat iron.

Group C: The tresses of Group C were shampooed with a standard shampoo. After rinsing the shampoo from the tresses, Inventive Formulation #1 (Example 1) was applied to the tresses and allowed to remain on the tresses for 4 minutes. After 4 minutes, without rinsing Inventive Formulation #1 from the tresses, a standard conditioner was applied to the tresses (layered onto the conditioner), followed by rinsing. The tresses were then blow dried.

Group D: The tresses of Group D were shampooed with TRESemme® shampoo and then conditioned with TRE-Semme® conditioner. After rinsing the conditioner from the hair, a commercial benchmark product (TRESemme® Leave-In Treatment) was applied to the hair. The commercial benchmark product was not rinsed from the hair, per the instructions of the commercial benchmark product. The hair was then blow dried.

Group E: The tresses of Group E were shampooed with a pure cleansing shampoo that is commonly used as a control in cosmetic testing. The hair was then blow dried.

The treatments of Groups A-E described above are summarized in the following table.

|  | Pure Cleansing Shampoo | Standard Shampoo | TRESemme® Shampoo | Standard Conditioner | TRESemme® Conditioner | Inventive Treatment #1 | TRESemme® Leave-In | Styling |
|---|---|---|---|---|---|---|---|---|
| Group A (Comparative) |  | X |  | X |  |  |  | Blow Dried |
| Group B (Comparative) |  | X |  | X |  |  |  | Blow Dried & Flat Iron |
| Group C (Inventive) |  | X |  | X |  | X |  | Blow Dried |
| Group D (Comparative) |  |  | X |  | X |  | X | Blow Dried |
| Group E (Control) | X |  |  |  |  |  |  | Blow Dried |

An Instron tensile tester was used to measure the frictional forces while each hair tress was pulled through a comb. The procedure was carried out in accordance with the widely-used method first proposed by Garcia & Diaz, *Combability Measurements on Hair*, JSCC, 27: 379-398 (1976). The combing experiments were performed in the wet state after the treatments outlined above. After swatches were blow dried and/or flat ironed, they were then immersed in deionized water for 10 minutes (1 at a time). Then the swatches were placed on an apparatus with a stationary comb and the maximum load ("wet combing") was measured. For dry combing, the maximum load was measured directly after blow drying and/or flat ironing. Six combing strokes were performed per tress, while eight replicate hair tresses were used per group to ensure statistical relevance.

Figure 3:
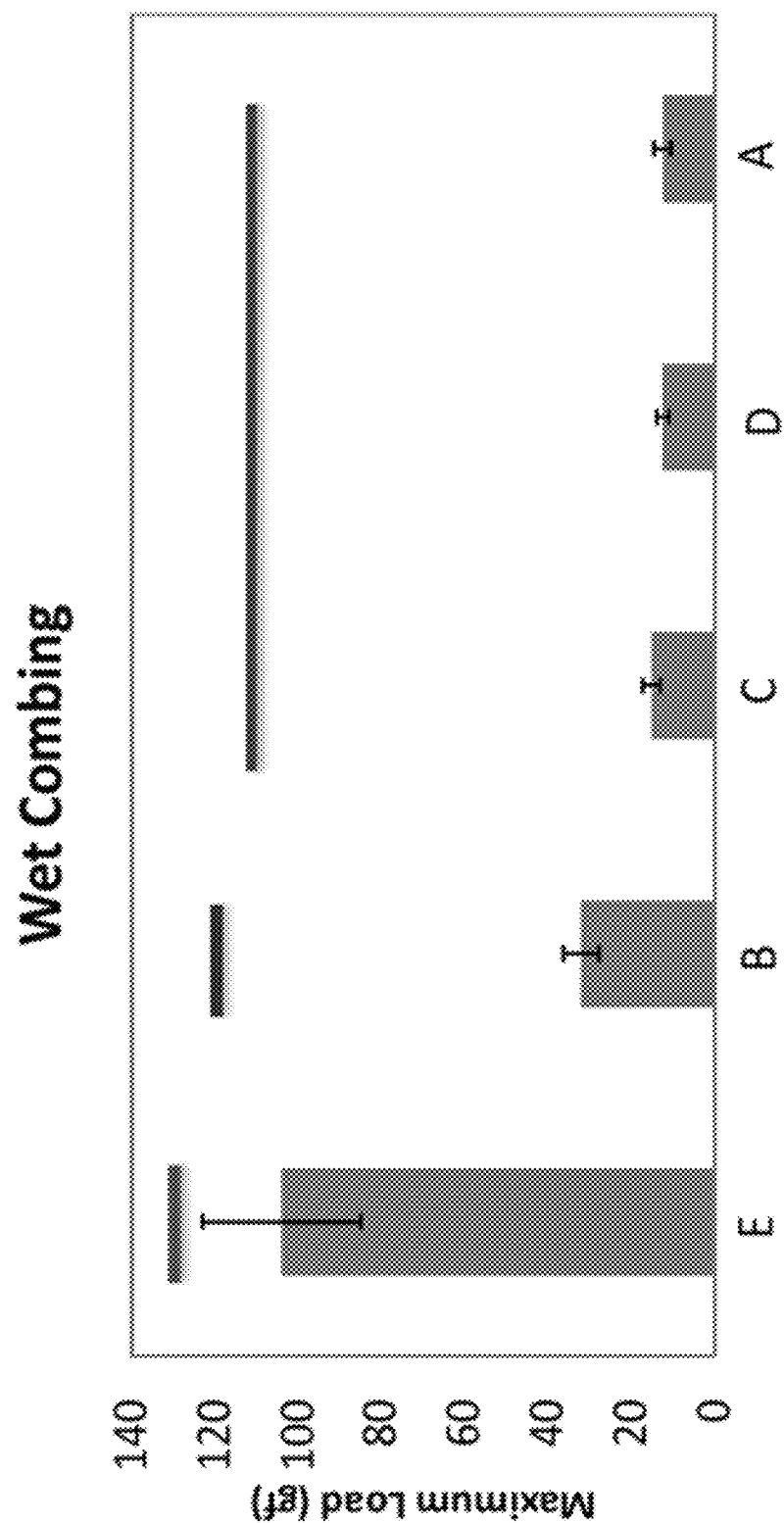
FIG. 3 is a bar graph comparing wet combing properties of (A) hair tresses treated with a standard shampoo and a standard conditioner; (B) hair tresses treated with a standard shampoo and a standard conditioner, and styled with a flat iron; (C) tresses treated with a standard shampoo and standard conditioner in conjunction with Inventive Formulation #6; (D) tresses treated with a commercial shampoo and commercial conditioner in conjunction with a commercial benchmark product; and (E) control tresses.

A lower maximum load force indicates easier combing (better surface properties). The results are provided in the table below in descending order of mean maximum load force. The results are also shown graphically in FIG. 3.

| Treatment Group | Mean Maximum Load (gf) |
|---|---|
| Group E | 104 |
| Group B | 32 |
| Group C | 15 |
| Group D | 12 |
| Group A | 12 |

Tresses of inventive Group C had statistically significant lower force (better combing properties) than tresses of control group E and tresses of comparative group B. There was no statistically significant difference between the forces for tresses of Group C, D, and A. This data shows that treating hair with inventive formulation #1 results in a statistically significant improvement in wet hair combing properties.

Example 8

Dry Combing Testing with Formulation #1

Testing was carried out to determine the dry combing properties of control hair tresses, tresses treated with Inventive Formulation #1 (Example 1), and tresses treated with a commercial benchmark product (TRESemme® Leave-In Product). Forty (40) natural wavy brown hair tresses (from IHIP) were separated into 8 groups of 6 tresses each, and treated as follows:

Group A: The tresses of Group A were shampooed with a standard shampoo and then conditioned with a standard conditioner. The tresses were then blow dried.

Group B: The tresses of Group B were shampooed with a standard shampoo and then conditioned with a standard conditioner. The tresses were blow dried and then styled with a flat iron.

Group C: The tresses of Group C were shampooed with a standard shampoo. After rinsing the shampoo from the tresses, Inventive Formulation #1 (Example 1) was applied to the tresses and allowed to remain on the tresses for 4 minutes. After 4 minutes, without rinsing Inventive Formulation #1 from the tresses, a standard conditioner was applied to the tresses (layered onto the conditioner), followed by rinsing. The tresses were then blow dried.

Group D: The tresses of Group D were shampooed with TRESemme® shampoo and then conditioned with TRESemme® conditioner. After rinsing the conditioner from the hair, a commercial benchmark product (TRESemme® Leave-In Treatment) was applied to the hair. The commercial benchmark product was not rinsed from the hair, per the instructions of the commercial benchmark product. The hair was then blow dried.

Group E: The tresses of Group E were shampooed with a pure cleansing shampoo that is commonly used as a control in cosmetic testing. The hair was then blow dried.

The treatments of Groups A-E described above are summarized in the following table.

|  | Pure Cleansing Shampoo | Standard Shampoo | TRESemme® Shampoo | Standard Conditioner | TRESemme® Conditioner | Inventive Treatment #1 | TRESemme® Leave-In | Styling |
|---|---|---|---|---|---|---|---|---|
| Group A (Comparative) |  | X |  | X |  |  |  | Blow Dried |
| Group B (Comparative) |  | X |  | X |  |  |  | Blow Dried & Flat Iron |
| Group C (Inventive) |  | X |  | X |  | X |  | Blow Dried |
| Group D (Comparative) |  |  | X |  | X |  | X | Blow Dried |
| Group E (Control) | X |  |  |  |  |  |  | Blow Dried |

Figure 4:
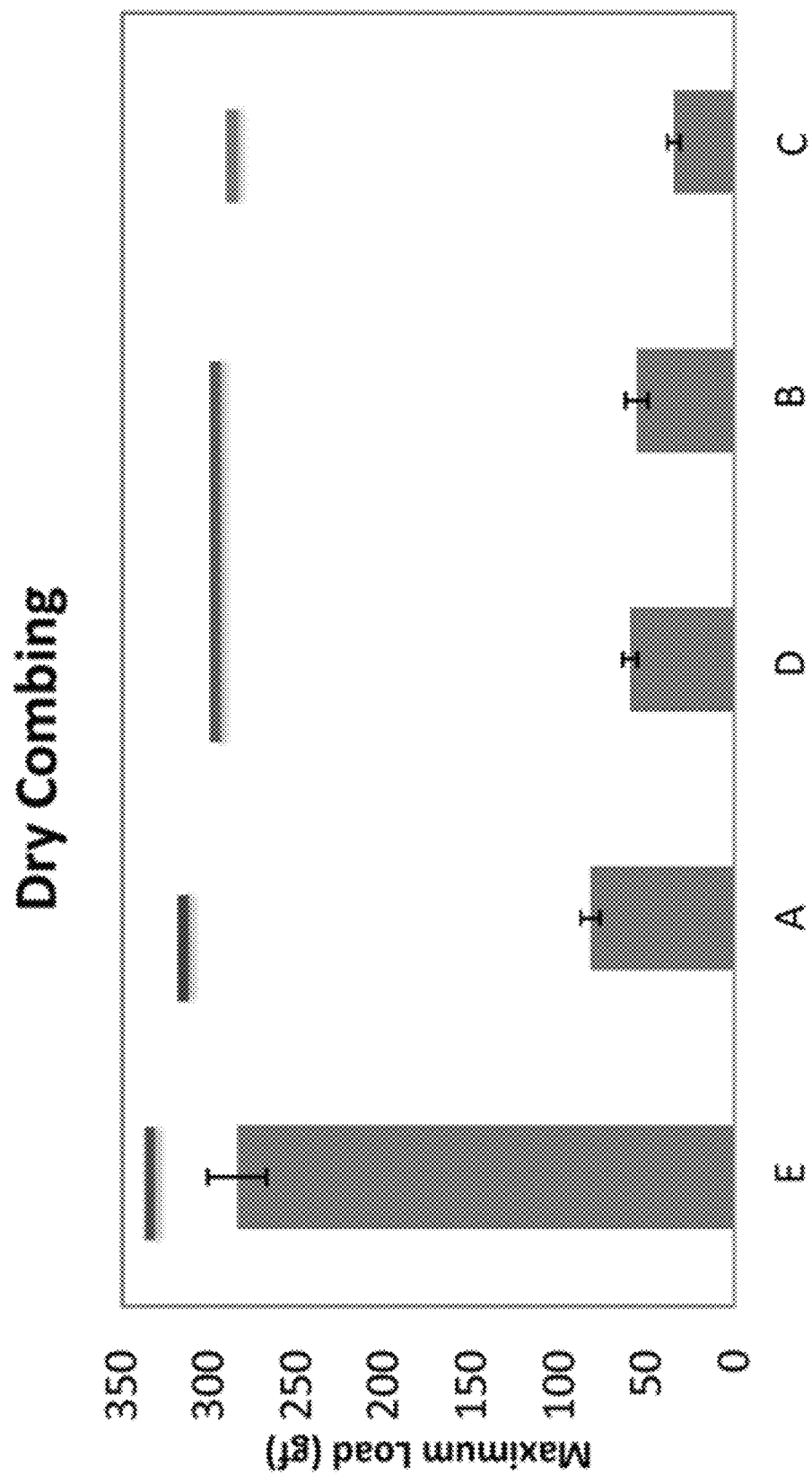
FIG. 4 is a bar graph comparing dry combing properties of (A) hair tresses treated with a standard shampoo and a standard conditioner; (B) hair tresses treated with a standard shampoo and a standard conditioner, and styled with a flat iron; (C) tresses treated with a standard shampoo and standard conditioner in conjunction with Inventive Formulation #6; (D) tresses treated with a commercial shampoo and commercial conditioner in conjunction with a commercial benchmark product; and (E) control tresses.

A lower maximum load force indicates easier combing (better surface properties). The results are provided in the table below in descending order of mean maximum load force. The results are also shown graphically in FIG. 4.

| Treatment Group | Mean Maximum Load (gf) |
| --- | --- |
| Group E | 284 |
| Group A | 82 |
| Group D | 60 |
| Group B | 56 |
| Group C | 35 |

Tresses of inventive Group C had statistically significant lower force (better combing properties) than tresses of all other groups. This data shows that treating hair with inventive formulation #1 results in a statistically significant improvement in dry hair combing properties.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" is equivalent to "mixtures thereof." Throughout the disclosure, the term "a mixture thereof" may be used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included in a mixture). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions can be modified with the "about," meaning within +/−5% of the indicated number.

Some of the various categories of components identified for the hair-treatment compositions may overlap. In such cases where overlap may exist between two or more components, a single overlapping compound does not represent more than one component. For example, a homopolymer of methyl quaternized dimethylaminoethyl methacrylate may be characterized as both a cationic polymer component and a thickening agent component. If a particular hair-treatment composition is described as including both a cationic polymer and a thickening agent, a single homopolymer of methyl quaternized dimethylaminoethyl methacrylate can serve as only the cationic polymer or only the thickening agent (the compound does not serve as both the cationic polymer and the thickening agent in the same composition).

All percentages, parts and ratios herein are based upon the total weight of the compositions of the present invention, unless otherwise indicated.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat," and its grammatical variations, relates to contacting hair with the hair-treatment compositions of the present disclosure.

The term "rinse," in the context of the instant disclosure, is used as customarily understood in the hair-care/hair-treatment art. For example, when a hair-treatment composition (e.g., a shampoo, conditioner, etc.) is "rinsed" from the hair, it is understood that at least some or most of the hair-treatment composition is removed from the hair. Nonetheless, in many cases, at least a residual amount of the hair-care composition or ingredient(s) from the hair care composition remains in or on the hair. In fact, in some cases, the residual amount of remaining composition or ingredient(s) is at least in part responsible for one or more of the styling benefits imparted to the hair.

A "rinse-off" hair-treatment composition refers to a composition that is rinsed and/or washed with water either after or during the application of the composition onto the hair, and before drying and/or styling the hair. At least a portion, and typically most, of the composition is removed from the hair during the rinsing and/or washing.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

The term "essentially anhydrous" or "substantially anhydrous" as used herein, for example, in the context of an "essentially anhydrous hair-treatment composition" or a "substantially anhydrous hair-treatment composition" means that the composition includes less than about 5% by weight of water. Nonetheless, the composition may include less than about 4 wt. %, less than about 3 wt. %, less than about 2 wt. %, less than about 1 wt. %, less than about 0.5 wt. %, less than about 0.1 wt. % of water, less than about 0.05 wt. % water, or less than 0.01 wt. % water.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair-treatment composition in the form of a gel comprising:
    about 0.01 to about 10 wt. % of polyurethane-34;
    about 0.01 to about 10 wt. % of one or more thickening agents selected from methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, methylhydroxypropyl starch, and a mixture thereof;
    about 0.1 to about 50 wt. % of one or more water soluble solvents;
    5 to 25% of dimethicone; and
    water;
    wherein the percentages by weight are based on the total weight of the composition.

2. A hair treatment composition of claim 1, wherein the one or more water-soluble solvents are selected from the group consisting of polyhydric alcohols, glycol ethers, $C_{1-4}$ alcohols, glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof.

3. A method for treating hair comprising applying a hair-treatment composition of claim 1 to the hair.

4. A hair-treatment composition of claim 1, further comprising:
    about 0.01 to about 10 wt. % of one or more cationic polymers.

5. A hair-treatment composition of claim 4, wherein the one or more cationic polymers are chosen from poly(methacryloyloxyethyl trimethylammonium chloride), polyquaternium-37, quaternized cellulose derivatives, polyquaternium-4, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof.

6. A hair-treatment composition of claim 4, wherein the one or more cationic polymers comprises polyquaternium-11.

7. A hair-treatment composition in the form of a gel comprising:
    about 0.01 to about 10 wt. % of polyurethane-34;
    about 0.01 to about 10 wt. % of one or more thickening agents selected from methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, methylhydroxypropyl starch, and a mixture thereof;
    about 0.1 to about 10 wt. % of one or more water soluble solvents;
    5 to 25% of dimethicone; and
    about 15 to about 90 wt. % of water;
    wherein the composition is free of waxes and the percentages by weight are based on the total weight of the composition.

8. A hair-treatment composition of claim 7, further comprising:
    about 0.01 to about 10 wt. % of one or more cationic polymers.

9. A hair-treatment composition of claim 8, wherein the one or more cationic polymers are chosen from poly(methacryloyloxyethyl trimethylammonium chloride), polyquaternium-37, quaternized cellulose derivatives, polyquaternium-4, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof.

10. A hair-treatment composition of claim 8, wherein the one or more cationic polymers comprises polyquaternium-11.

* * * * *